United States Patent
Pais et al.

(10) Patent No.: US 11,578,311 B2
(45) Date of Patent: Feb. 14, 2023

(54) AVOIDING EPIGENETIC SILENCING OF EXOGENOUS NUCLEIC ACID IN ALGAE

(71) Applicant: Synthetic Genomics, Inc., La Jolla, CA (US)

(72) Inventors: June Elizabeth Pais, San Diego, CA (US); Roberto Spreafico, La Jolla, CA (US)

(73) Assignee: Viridos, Inc., La Jolla, CA (US)

( * ) Notice: Subject to any disclaimer, the term of this patent is extended or adjusted under 35 U.S.C. 154(b) by 439 days.

(21) Appl. No.: 16/711,944

(22) Filed: Dec. 12, 2019

(65) Prior Publication Data
US 2020/0190485 A1 Jun. 18, 2020

Related U.S. Application Data

(60) Provisional application No. 62/779,364, filed on Dec. 13, 2018.

(51) Int. Cl.
| | | |
|---|---|---|
| *C12N 9/10* | (2006.01) | |
| *C12N 15/90* | (2006.01) | |
| *A01H 13/00* | (2006.01) | |

(52) U.S. Cl.
CPC ......... *C12N 9/1007* (2013.01); *C12N 15/902* (2013.01); *C12Y 201/01037* (2013.01); *C12N 2310/20* (2017.05); *C12N 2800/80* (2013.01)

(58) Field of Classification Search
None
See application file for complete search history.

(56) References Cited

U.S. PATENT DOCUMENTS

2012/0311737 A1 12/2012 Grimanelli et al.

OTHER PUBLICATIONS

EP Extended European Search Report in European Application No. 19895510, dated Jul. 29, 2022, 8 pages.
Kim et al., "Gene silencing in microalgae: Mechanisms and biological roles", Bioresources Technology, Oct. 30, 2014, 184:23-32.
Kurniasih et al., "UV-mediated Chlamydomonas mutants with enhanced nuclear transgene expression by disruption of DNA methylation-dependent and independent silencing systems", Plant Molecular Biology, Oct. 19, 2016, 92(6):629-641.
Underwood et al., "Epigenetic activation of meiotic recombination near *Arabidopsis thaliana* centromeres via loss of H3K9me2 and non-CG DNA methylation", Genome Research, Apr. 2, 2018, 28(4):519-531.
Barney, B. M. et al.: "*DNA (cytosine-5)-methyltransferase CMT1 isoform A [Chlorella sorokiniana]*"; National Center for Biotechnology Information. Genbank Entry, Feb. 2, 2018 [retrieved on Mar. 17, 2020]. Retrieved from the Internet: <URL: https://www.ncbi.nlm.nih.gov/protein/PRW44284>; pp. 1-2.
Bartee, L. et al.: "*Arabidopsis CMT3 Chromomethylase Mutations Block Non-CG Methylation and Silencing of an Endogenous Gene*"; Genes and Development, Jul. 15, 2001; vol. 15, No. 14, pp. 1753-1758.
Du, Jiamu et al.: "*DNA methylation pathways and their crosstalk with histone methylation*"; Nat Rev Mol Cell Biol., Sep. 2015; 16(9): 519-532.
Finnegan, E. J. et al.: "*DNA Methylation in Plants*"; Annual Reviews of Plant Physiology and Plant Molecular Biology, Jun. 1998; vol. 49; pp. 223-247.
Gonzalez, R. M. et al.: "*Atypical Epigenetic Markin an Atypical Location: Cytosine Methylation at Asymmetric (CNN) Sites within the Body of a Non-Repetitive Tomato Gene*"; BMC Plant Biology. 2011; vol. 11, No. 94; pp. 1-11.
International Search Report dated Apr. 27, 2020, regarding PCT/US2019/065879.
Jia, Yan-Long et al.: "*CRISPR/Cas9-mediated Gene Knockout for DNA Methyltransferase Dnmt3a in CHO Cells Displays Enhanced Transgenic Expression and Long-Term Stability*"; Journal of Cellular and Molecular Medicine, May 30, 2018; vol. 22, No. 9; pp. 4106-4116.
Lindroth, A. M. et al.: "*Dual Histone H3 Methylation Marks at Lysines 9 and 27 Required for Interaction with Chromomethylase3*" The EMBO Journal, Sep. 30, 2004; vol. 23, No. 21; pp. 4286-4296.

*Primary Examiner* — Suzanne M Noakes
*Assistant Examiner* — Jae W Lee
(74) *Attorney, Agent, or Firm* — DLA Piper LLP (US)

(57) ABSTRACT

The present application relates to the identification of novel DNA methyltransferases including CHG methylation in algal species. The present application relates to algal mutants permitting the expression of exogenous genes by alleviating the epigenetic mechanisms of CHG and CHH methylation of exogenous DNA and mono- and tri-methylation of lysine 9 of histone 3 (H3K9). This is achieved by mutating or attenuating the methyltransferase (MTase) genes in algae. The present application also relates to methods for efficiently expressing exogenous genes in algal species.

23 Claims, 9 Drawing Sheets

Specification includes a Sequence Listing.

AVOIDING EPIGENETIC SILENCING OF EXOGENOUS NUCLEIC ACID IN ALGAE

CROSS-REFERENCE TO RELATED APPLICATIONS

This application claims benefit of priority under 35 U.S.C. § 119 (e) of U.S. Ser. No. 62/779,364, filed Dec. 13, 2018, the entire contents of which is incorporated herein by reference in its entirety.

INCORPORATION OF SEQUENCE LISTING

The material in the accompanying sequence listing is hereby incorporated by reference into this application. The accompanying sequence listing text file, name SGI2210_1_Sequence_Listing.txt, was created on Dec. 11, 2019, and is 79 kb. The file can be accessed using Microsoft Word on a computer that uses Windows OS.

FIELD OF THE INVENTION

The present application relates algal mutants permitting the expression of exogenous genes by alleviating the epigenetic mechanisms of methylation of exogenous DNA. This is achieved by mutating or attenuating the methyltransferase (MTase) genes in algae. The present application also relates to methods for efficiently expressing exogenous genes in algal species.

BACKGROUND

Methylation of DNA is a common epigenetic signaling tool that cells use to lock genes in the "off" position. Generally, DNA methylation occurs at the cytosine bases of eukaryotic DNA, which are converted to 5-methylcytosine by DNA methyltransferase (DNMT) enzymes. DNA methylation can be categorized into three types according to the sequence context of the cytosines, namely CG, CHG, and CHH (H=A, C, or T). Typically, in eukaryotes, methylation is found sparsely but globally, distributed in definite CpG sequences throughout the entire genome, with the exception of CpG islands.

Methylation of cytosine is more prevalent in CpG sequences than in CHG or CHH sequences in the algal species *Chlamydomonas reinhardtii* (Feng. et al., Proc. Natl. Acad. Sci. U.S.A. 2010 May 11; 107(19):8689-94).

Aside from methylation of DNA, methylation of histone can silence a gene as well. For example, mono-methylation of lysine in histone 3 (H3K9) has been found to mark transgene tandem repeats in *Chlamydomonas reinhardtii*. SET3, an H3K9 monomethyltransferase was identified as involved in the methylation of H3K9. The role of H3K9 mono-, di- and trimethylation is species-specific and serves distinct functions (Caras-Mollano et al., Nucleic Acids Res. 2007; 35(3):939-50)

SUMMARY

Provided herein are algal mutants permitting the expression of exogenous genes by alleviating the epigenetic mechanisms of methylating exogenous or foreign DNA. In some embodiments, the methyltransferase is a CHG DNA methyltransferase. In some embodiments, the methyltransferase is a CHH DNA methyltransferase. Also provided are methods for efficiently expressing exogenous DNA in algal species.

CHG methylation (and silencing) has been observed when certain exogenous genes are expressed in an organism. Moreover, targeting the MTase genes offers an advantage in that it is specific for targeting the silencing mechanism without having to deploy other tools for gene refactoring.

In one aspect, provided are mutant photosynthetic organism comprising a mutated or attenuated gene encoding a polypeptide having a CHG DNA methyltransferase activity. The mutant photosynthetic microorganism has reduced CHG DNA methylation as compared to a control photosynthetic organism without a mutated or attenuated gene encoding a polypeptide having a CHG DNA methyltransferase activity.

In one aspect, provided are methods of enhancing the expression of an exogenous DNA in a photosynthetic organism. The methods include a) introducing an exogenous DNA into the photosynthetic organism; b) mutating or attenuating the gene encoding a polypeptide having a CHG DNA methyltransferase activity in which the mutant microorganism has reduced CHG DNA methylation of the exogenous DNA as compared to a control photosynthetic organism in which the control organism comprises the exogenous DNA but without a mutated or attenuated gene encoding a polypeptide having a CHG DNA methyltransferase activity such that the expression of the exogenous DNA is enhanced in the photosynthetic organism as compared to the control photosynthetic organism.

In one aspect, provided are methods of reducing the methylation (e.g., monomethylation, trimethylation) of lysine 9 on histone H3 (H3K9) in a photosynthetic organism. The methods include mutating or attenuating the gene encoding a polypeptide having a CHG DNA methyltransferase activity, wherein the mutant microorganism has reduced CHG DNA methylation as compared to a control photosynthetic organism without a mutated or attenuated gene encoding a polypeptide having a CHG DNA methyltransferase activity; wherein the monomethylation of lysine 9 on histone H3 (H3K9me1) or trimethylation of lysine 9 on histone H3 (H3K9me3) of the photosynthetic organism is reduced.

In some embodiments, the mutant photosynthetic organism is a genetically engineered mutant. In some embodiments, the mutant has been genetically engineered by insertional mutagenesis, gene replacement, RNAi, antisense RNA, meganuclease genome engineering, one or more ribozymes, and/or a CRISPR/Cas system. In some embodiments, the mutant has been genetically engineered by a CRISPR/Cas system. In some embodiments, the mutant photosynthetic organism has been generated by UV irradiation, gamma irradiation, or chemical mutagenesis.

In some embodiments, the mutant photosynthetic organism comprises a mutation or attenuation in a gene that encodes a polypeptide having a CHG DNA methyltransferase activity comprising an amino acid sequence having at least 65% identity to an amino acid sequence of SEQ ID NO: 1 or SEQ ID NO: 28 prior to the mutation or attenuation of the gene. In some embodiments, the polypeptide having a CHG DNA methyltransferase activity comprises an amino acid sequence having at least 80% identity to an amino acid sequence of SEQ ID NO: 1 or SEQ ID NO: 28 prior to the mutation or attenuation of the gene.

In some embodiments, the mutant photosynthetic organism comprises an exogenous DNA, and wherein the reduced CHG DNA methylation is in the exogenous DNA. In some embodiments, the exogenous DNA is integrated into the genome of the photosynthetic organism.

In some embodiments the reduced CHG DNA methylation can be in a DNA sequence native to the photosynthetic organism. The reduced DNA methylation can be in the centromere or in a highly repetitive DNA region of the mutant photosynthetic organism.

In some embodiments, the expression of the exogenous nucleic acid is improved (e.g. increased) compared to a control photosynthetic organism in which the control organism comprises comprising the exogenous nucleic acid but without a mutated or attenuated gene encoding a polypeptide having a CHG DNA methyltransferase activity.

In some embodiments, the mutant photosynthetic organism has reduced methylation (e.g., monomethylation, trimethylation) of lysine 9 of histone H3 (H3K9). In some embodiments, the mutant photosynthetic organism has reduced CHH DNA methylation as compared to a control photosynthetic organism in which the control organism is without a mutated or attenuated gene encoding a polypeptide having a CHG DNA methyltransferase activity.

In some embodiments, the photosynthetic organism is algae. In some embodiments, the algae belong to genus *Achnanthes, Amphiprora, Amphora, Ankistrodesmus, Asteromonas, Boekelovia, Bolidomonas, Borodinella, Botrydium, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Eustigmatos, Franceia, Fragilaria, Gloeothamnion, Haematococcus, Halocafeteria, Heterosigma, Hymenomonas, Isochrysis, Lepocinclis, Micractinium, Monodus, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Pelagomonas, Phaeodactylum, Phagus, Picochlorum, Platymonas, Pleurochrysis, Pleurococcus, Prototheca, Pseudochlorella, Pseudoneochloris, Pseudostaurastrum, Pyramimonas, Pyrobotrys, Scenedesmus, Skeletonema, Spyrogyra, Stichococcus, Tetraselmis, Thalassiosira, Tribonema, Vaucheria, Viridiella, Vischeria,* and *Volvox*. In some embodiments, the mutant photosynthetic organism is a Chlorophyte or Charophyte alga. In some embodiments the organism can be, for example, an alga of any of the classes Chlorophyceae, Trebouxiophyceae, Chlorodendrophyceae, Ulvophyceae, Pedinophyceae, or Prasinophyceae. The organism can be a member of the family Chlorellales, or family Oocystaceae, or family Chlorodendraceae. In some embodiments, the mutant algal cell is a Chlorophyte algal cell of the Trebouxiophyceae class, for example, an algal cell of a species of a genus such as *Botryococcus, Chlorella, Auxenochlorella, Heveochlorella, Marinichlorella, Parachlorella, Pseudochlorella, Tetrachlorella, Eremosphaera, Franceia, Micractinium, Nannochloris, Oocystis, Picochlorum,* or *Prototheca*. In some embodiments, the mutant alga can be a mutant alga of a species of *Auxenochlorella, Chlorella, Heveochlorella, Marinichlorella, Parachlorella, Pseudochlorella* or *Tetrachlorella*. In other embodiments the mutant alga can be an alga of the Class Chlorodendrophyceae (e.g. of the genus *Tetraselmis*).

In some embodiments, the mutant photosynthetic microorganism is a cyanobacterium. In some embodiments, the cyanobacterium is an *Acaryochloris, Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, thermosynechocystis, Tolypothrix, Trichodesmium, Tychonema,* or *Xenococcus* species.

BRIEF DESCRIPTION OF THE DRAWINGS

FIG. 8A shows strain STR24194 (a background strain) for five Cre constructs. FIG. 8B shows the same data for *Oocystis* sp. having a deletion of the sequence encoding the methyltransferase of SEQ ID NO: 28 (STR29997). The data show that the cre recombinase transgene is expressed in *Oocystis* sp. background strain (STR24194).

DETAILED DESCRIPTION OF THE INVENTION

Figure 1:
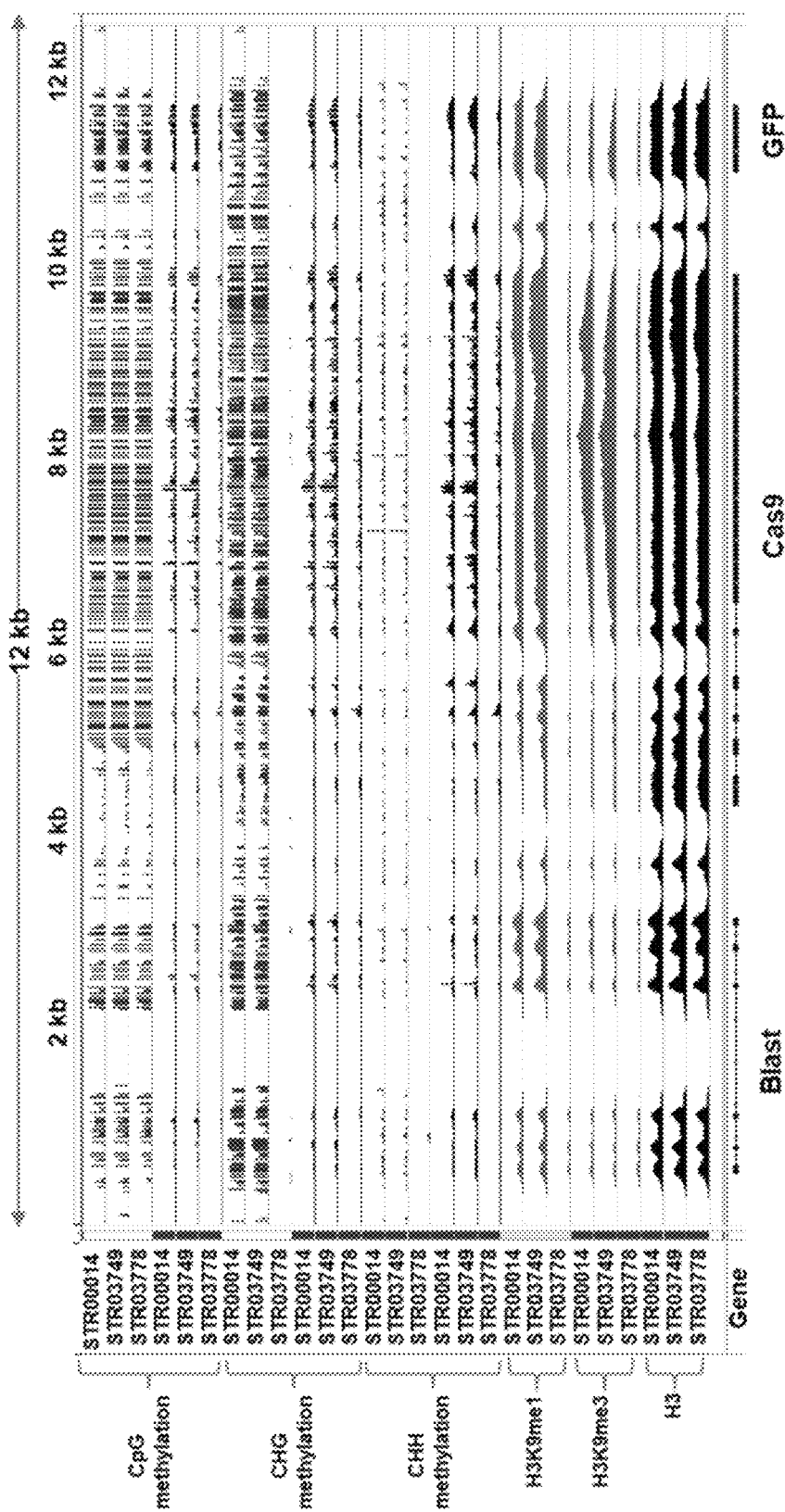
FIG. 1 is a genome track showing the presence of CpG, CHG, and CHH DNA methylation and H3K9 mono and trimethylation of exogenous DNA integrated into the *Parachlorella* sp. genome, and the reduction of these methylations by knocking out the CHG methyltransferase. The exogenous DNA methylation and H3K9 monomethylation and trimethylation status of the *Parachlorella* knockout strains STR03778 and STR03749 were compared with the *Parachlorella* control strain STR00014. Table 1 further identifies these strains. All three strains comprise the integrated blasticidin, Cas-9, and GFP genes. Representative exogenous DNA genome tracks comprising the blasticidin, Cas-9, and GFP genes depicting the percent DNA methylation (first set of rows) and the genome coverage (second set of rows) were shown, as well as the sequence information from chromatin immunoprecipitation (ChIPs) with three *Parachlorella* strains isolated with antibodies specific for H3K9me1 and H3K9me3. Tracks are scaled to allow comparison across different samples. The coverage tracks for histone 3 (H3) are also shown. The chromosome position is shown at the top, and the gene models are provided at the bottom.

The present application discloses the epigenetic mechanism of silencing the expression of exogenous genes in algae. The present application identifies the role of CHG methylation of exogenous DNA in epigenetic silencing in algae. As such, the role of CHG methylation in exogenous gene silencing is generally unknown in algae, either because CHG methylation is absent altogether even from endogenous elements (*Chlamydomonas, Volvox*) or because only native but not exogenous DNA elements were examined (*Chlorella*). Additionally, the present application also identifies the role of the role of histone 3, lysine 9 (H3K9) methylation (e.g., monomethylation or trimethylation) in epigenetic silencing of exogenous genes in algal species.

The present application identifies novel putative methyltransferase genes (Pfam PF00145, C-5 cytosine-specific DNA methyltransferases) in Trebouxiophyceae algae. The activities of the newly identified genes were analyzed by individually knocking out genes and evaluating the effect of the knockouts on methylation of DNA in native and exogenous DNA sequences and the level of protein expression of the exogenous genes. Disclosed is the effect of these knockouts on methylation of cytosine in CpG, CHG, and CHH DNA sequences, where H=A, T, or C. Also disclosed is the level of methylation (e.g., monomethylation, trimethylation) of histone 3, lysine 9 (H3K9) in the chromatin regions of the native DNA as well as the chromatin regions comprising exogenous DNA. Also disclosed is an orthologous CHG DNA methyltransferase in *Oocystis* sp.

The present inventors discovered unexpectedly that mutating or attenuating a DNA methyltransferase reduces the CHG and/or CHH methylation of exogenous DNA, which can occur by epigenetic mechanisms. The present inventors also discovered that mutating or attenuating the DNA methyltransferase enhances the level of protein expression of exogenous genes. Additionally, the level of monomethylation and trimethylation of histone 3, lysine 9 (H3K9) in the chromatin regions comprising exogenous DNA is also reduced. It was further discovered that mutating or attenuating the DNA methyltransferase reduces the CHH methylation of exogenous DNA. The invention therefore provides mutant Chlorophyte algae having an attenuation of at least one CHG and/or CHH methyltranferase as disclosed herein.

DNA methylation of exogenous DNA in Chlorophyte algae can involve DNA methylation in a CHG sequence, where "C" is the methylated cytosine, and "H" is an A, T, or C). In various embodiments the mutant photosynthetic organism of the invention can have an attenuation or deletion of at least one gene encoding a methyltransferase. In some embodiments the encoded methyltransferase is any of SEQ ID NO: 1, 3, 5, 7, 28, or any combination or sub-combination of them, or a sequence encoding a variant of them and having at least 80% or at least 90% or at least 95% or at least 97% or at least 98% or 100% amino acid sequence identity with any of them, or to fragments thereof comprising a consecutive sequence of at least 50 or at least 100, at least 125, at least 150 or more amino acid residues of the entire protein, or to any combination or sub-combination of them. In other embodiments the methyltransferase is encoded by any sequence or variant thereof, disclosed herein.

The invention also involves methods of enhancing the expression of exogenous DNA in a mutant photosynthetic organism of the invention. The methods involve a) introducing an exogenous DNA into the photosynthetic organism; and b) mutating, attenuating, or deleting a gene encoding a polypeptide having a CHG and/or CHH DNA methyltransferase activity. The exogenous DNA introduced into the organism can be a DNA construct containing sequences for editing, attenuating, or deleting the gene encoding the methyltransferase activity. The mutation, attenuation, or deletion of the sequence can be accomplished by any suitable method known to persons of ordinary skill in the art. For example a CRISPR Cas9 gene editing, Cre-Lox recombination, or other gene editing technology can be used. The mutant organism produced by the method can have reduced CHG and/or CHH DNA methylation of the exogenous DNA as compared to a control photosynthetic organism having the exogenous DNA but not the mutated or attenuated gene encoding a polypeptide having a CHG and/or CHH DNA methyltransferase activity. Thus, the expression of the exogenous DNA is enhanced in the mutated organism as compared to the control organism. The encoded methyltransferase mutated, attenuated, or deleted in the organism can be any of SEQ ID NO: 1, 3, 5, 7, 28 or any combination or sub-combination of them, or a (variant) sequence of them and having at least 80% or at least 90% or at least 95% or at least 97% or at least 98% or 100% sequence identity with any of them, or to fragments thereof comprising a consecutive sequence of at least 50 or at least 100, at least 125, at least 150 or more amino acid residues of the entire protein or nucleotides of a nucleic acid sequence, or any combination or sub-combination of them. In other embodiments the methyltransferase is encoded by any sequence or variant thereof, disclosed herein. For example the methyltransferase can be encoded by any of SEQ ID NO: 2, 4, 6, 8, or 29, or a (variant) sequence of them and having at least 80% or at least 90% or at least 95% or at least 97% or at least 98% or 100% sequence identity with any of them, or to fragments thereof comprising a consecutive sequence of at least 200, at least 300, at least 500 or more nucleotide residues of the entire nucleic acid sequence, or any combination or sub-combination of them. In some embodiments the reduction in CHG and/or CHH methylation occurs in highly repetitive regions of exogenous DNA and/or at centromere regions of exogenous DNA. Highly repetitive regions or sequences of DNA normally do not code for polypeptides. In some embodiments the highly repetitive regions or sequences are short sequences of 5-100 or 150-300 nucleotides. In some embodiments the sequence repeats at least 10,000 times, or at least 50,000 times, or at least 100,000 times or at least 500,000 times or at least 1 million times in the region of DNA. The region can be a chromosome or can be a section of DNA of less than 1 Mb or less than 25 Mb or less than 50 Mb or less than 100 Mb or less than 250 Mb.

Definitions

Unless defined otherwise, all technical and scientific terms used herein have the same meaning as commonly understood by one of ordinary skill in the art to which this invention belongs. In case of conflict, the present application including the definitions will control. Unless otherwise required by context, singular terms shall include pluralities and plural terms shall include the singular. All ranges provided within the application are inclusive of the values of the upper and lower ends of the range unless specifically indicated otherwise.

All publications, patents and other references mentioned herein are incorporated by reference in their entireties for all purposes as if each individual publication or patent application were specifically and individually indicated to be incorporated by reference.

The term "and/or" as used in a phrase such as "A and/or B" herein is intended to include "A and B", "A or B", "A", and "B".

"About" means either within 10% of the stated value, or within 5% of the stated value, or in some cases within 2.5% of the stated value, or, "about" can mean rounded to the nearest significant digit.

The term "gene" is used broadly to refer to any segment of a nucleic acid molecule (typically DNA, but optionally RNA) encoding a polypeptide or expressed RNA. Thus, genes include sequences encoding expressed RNA (which can include polypeptide coding sequences or, for example, functional RNAs, such as ribosomal RNAs, tRNAs, antisense RNAs, microRNAs, short hairpin RNAs, ribozymes, etc.). Genes may further comprise regulatory sequences required for or affecting their expression, as well as sequences associated with the protein or RNA-encoding sequence in its natural state, such as, for example, intron sequences, 5' or 3' untranslated sequences, etc. In some examples, "gene" may only refer to a protein-encoding portion of a DNA or RNA molecule, which may or may not include introns. A gene is preferably greater than 50 nucleotides in length, more preferably greater than 100 nucleotide in length, and can be, for example, between 50 nucleotides and 500,000 nucleotides in length, such as between 100 nucleotides and 100,000 nucleotides in length or between about 200 nucleotides and about 50,000 nucleotides in length, or about 200 nucleotides and about 20,000 nucleotides in length. Genes can be obtained from a variety of sources, including cloning from a source of interest or synthesizing from known or predicted sequence information.

The term "nucleic acid" or "nucleic acid molecule" refers to, a segment of DNA or RNA (e.g., mRNA), and also includes nucleic acids having modified backbones (e.g., peptide nucleic acids, locked nucleic acids) or modified or non-naturally-occurring nucleobases. The nucleic acid molecules can be double-stranded or single-stranded; a single-stranded nucleic acid molecule that comprises a gene or a portion thereof can be a coding (sense) strand or a non-coding (antisense) strand.

A nucleic acid molecule or polypeptide may be "derived from" an indicated source, which includes the isolation (in whole or in part) of a nucleic acid segment or polypeptide from an indicated source. A nucleic acid molecule may also be derived from an indicated source by, for example, direct cloning, PCR amplification, or artificial synthesis from the indicated polynucleotide source or based on a sequence associated with the indicated polynucleotide source, which may be, for example, a species of organism.

Genes or nucleic acid molecules derived from a particular source or species also include genes or nucleic acid molecules having sequence modifications with respect to the source nucleic acid molecules, that is, the sequence of the gene or nucleic acid molecule is derived from the sequence of a gene or nucleic acid molecule from the referenced source or species but may have modifications. For example, a gene or nucleic acid molecule derived from a source (e.g., a particular referenced gene) can include one or more mutations with respect to the source gene or nucleic acid molecule that are unintended or that are deliberately introduced, and if one or more mutations, including substitutions, deletions, or insertions, are deliberately introduced the sequence alterations can be introduced by random or targeted mutation of cells or nucleic acids, by amplification or other gene synthesis or molecular biology techniques, or by chemical synthesis, or any combination thereof. A gene or nucleic acid molecule that is derived from a referenced gene or nucleic acid molecule that encodes a functional RNA or polypeptide can encode a functional RNA or polypeptide having at least 65%, at least 70%, at least 75%, at least 80%, at least 85%, at least 90%, or at least 95%, sequence identity with the referenced or source functional RNA or polypeptide, or to a functional fragment thereof. For example, a gene or nucleic acid molecule that is derived from a referenced gene or nucleic acid molecule that encodes a functional RNA or polypeptide can encode a functional RNA or polypeptide having at least 85%, at least 90%, at least 95%, at least 96%, at least 97%, at least 98%, or at least 99% sequence identity with the referenced or source functional RNA or polypeptide, or to a functional fragment thereof.

Similarly, a polypeptide or protein derived from a particular source or species includes polypeptides or proteins having sequence modifications with respect to the source polypeptide, that is, the polypeptide is derived from the sequence of a polypeptide from the referenced source or species but may have modifications. For example, a polypeptide or protein derived from a source (e.g., a particular referenced protein) can include one or more mutations (amino acid differences) with respect to the source polypeptide that are unintended or that are deliberately introduced (for example, by mutation of the encoding nucleic acid molecule). A polypeptide that is derived from a referenced polypeptide can have at least 60%, at least 65%, at least 70%, at least 75%, at least 80%, at least 85%, at least 90%, or at least 95% sequence identity with the referenced or source polypeptide, or to a functional fragment thereof. For example, a polypeptide that is derived from a referenced polypeptide can have at least 80%, or at least 85%, at least 90%, at least 95%, at least 96%, at least 97%, at least 98%, or at least 99% sequence identity with the referenced or source polypeptide, or a functional fragment thereof.

The terms "naturally-occurring", "native", and "wild-type" refer to a form found in nature. For example, a naturally occurring or wild-type nucleic acid molecule, nucleotide sequence or protein may be present in, and isolated from a natural source and is not intentionally modified by human manipulation.

As used herein "attenuated" means reduced in amount, degree, intensity, or strength. Attenuated gene expression may refer to a significantly reduced amount and/or rate of transcription of the gene in question, or of translation, folding, or assembly of the encoded protein. As nonlimiting examples, an attenuated gene may be a mutated or disrupted gene (e.g., a gene disrupted by partial or total deletion, truncation, frameshifting, or insertional mutation) that does not encode a complete functional open reading frame or that has decreased expression due to alteration or disruption of gene regulatory sequences. An attenuated gene may also be a gene targeted by a construct that reduces expression of the gene, such as, for example, an antisense RNA, microRNA, RNAi molecule, or ribozyme. Attenuated gene expression can be gene expression that is eliminated, for example, reduced to an amount that is insignificant or undetectable. Attenuated gene expression can also be gene expression that results in an RNA or protein that is not fully functional or nonfunctional, for example, attenuated gene expression can be gene expression that results in a truncated RNA and/or polypeptide.

"Exogenous nucleic acid molecule", "transgene", or "exogenous gene" refers to a nucleic acid molecule or gene that has been introduced (e.g., transformed) into a cell. A transformed cell may be referred to as a recombinant cell, into which additional exogenous gene(s) may be introduced. A descendent of a cell transformed with a nucleic acid molecule is also referred to as "transformed" if it has inherited the exogenous nucleic acid molecule. An "endogenous" nucleic acid molecule, gene or protein is a native nucleic acid molecule, gene, or protein as it occurs in, or is naturally produced by, the host.

A "recombinant" or "engineered" nucleic acid molecule is a nucleic acid molecule that has been altered through human manipulation. As non-limiting examples, a recombinant nucleic acid molecule includes any nucleic acid molecule that: 1) has been partially or fully synthesized or modified in vitro, for example, using chemical or enzymatic techniques (e.g., by use of chemical nucleic acid synthesis, or by use of enzymes for the replication, polymerization, digestion (exonucleolytic or endonucleolytic), ligation, reverse transcription, transcription, base modification (including, e.g., methylation), integration or recombination (including homologous and site-specific recombination) of nucleic acid molecules); 2) includes conjoined nucleotide sequences that are not conjoined in nature; 3) has been engineered using molecular cloning techniques such that it lacks one or more nucleotides with respect to the naturally occurring nucleic acid molecule sequence; and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

The term "recombinant protein" as used herein refers to a protein produced by genetic engineering regardless of whether the amino acid varies from that of a wild-type protein.

When applied to organisms, the term recombinant, engineered, or genetically engineered refers to organisms that have been manipulated by introduction of a heterologous or exogenous recombinant nucleic acid sequence into the organism (e.g., a non-native nucleic acid sequence), and includes gene knockouts, targeted mutations, gene replacement, and promoter replacement, deletion, disruption, or insertion, as well as introduction of transgenes or synthetic genes or nucleic acid sequences into the organism. That is, recombinant, engineered, or genetically engineered refers to organisms that have been altered by human intervention. Recombinant or genetically engineered organisms can also be organisms into which constructs for reduced gene expression or gene "knockdown" have been introduced. Such constructs include, but are not limited to, RNAi, microRNA, shRNA, siRNA, antisense, and ribozyme constructs. Also included are organisms whose genomes have been altered by the activity of meganucleases, zinc finger nucleases, TALENs, or Cas/CRISPR systems. An exogenous or recombinant nucleic acid molecule can be integrated into the recombinant/genetically engineered organism's genome or in other instances may not be integrated into the host genome. As used herein, "recombinant microorganism" or "recombinant host cell" includes progeny or derivatives of the recombinant microorganisms of the invention. Because certain modifications may occur in succeeding generations due to either mutation or environmental influences, such progeny or derivatives may not, in fact, be identical to the parent cell, but are still included within the scope of the term as used herein.

The term "promoter" refers to a nucleic acid sequence capable of binding RNA polymerase in a cell and initiating transcription of a downstream (3' direction) coding sequence. A promoter includes the minimum number of bases or elements necessary to initiate transcription at levels detectable above background. A promoter can include a transcription initiation site as well as protein binding domains (consensus sequences) responsible for the binding of RNA polymerase. Eukaryotic promoters often, but not always, contain "TATA" boxes and "CAT" boxes. Prokaryotic promoters may contain −10 and −35 prokaryotic promoter consensus sequences. A large number of promoters, including constitutive, inducible and repressible promoters, from a variety of different sources are well known in the art.

Representative sources include for example, algal, viral, mammalian, insect, plant, yeast, and bacterial cell types, and suitable promoters from these sources are readily available, or can be made synthetically, based on sequences publicly available online or, for example, from depositories such as the ATCC as well as other commercial or individual sources. Promoters can be unidirectional (initiate transcription in one direction) or bi-directional (initiate transcription in either direction). A promoter may be a constitutive promoter, a repressible promoter, or an inducible promoter. A promoter region can include, in addition to the gene-proximal promoter where RNA polymerase binds to initiate transcription, additional sequences upstream of the gene that can be within 1 kb, 2 kb, 3 kb, 4 kb, 5 kb or more of the transcriptional start site of a gene, where the additional sequences can influence the rate of transcription of the downstream gene and optionally the responsiveness of the promoter to developmental, environmental, or biochemical (e.g., metabolic) conditions.

The term "heterologous" when used in reference to a polynucleotide, gene, nucleic acid, polypeptide, or enzyme refers to a polynucleotide, gene, nucleic acid, polypeptide, or enzyme that is from a source or derived from a source other than the host organism species. In contrast a "homologous" polynucleotide, gene, nucleic acid, polypeptide, or enzyme is used herein to denote a polynucleotide, gene, nucleic acid, polypeptide, or enzyme that is derived from the host organism species. When referring to a gene regulatory sequence or to an auxiliary nucleic acid sequence used for maintaining or manipulating a gene sequence (e.g. a promoter, a 5' untranslated region, 3' untranslated region, poly A addition sequence, intron sequence, splice site, ribosome binding site, internal ribosome entry sequence, genome homology region, recombination site, etc.), "heterologous" means that the regulatory sequence or auxiliary sequence is not naturally associated with the gene with which the regulatory or auxiliary nucleic acid sequence is juxtaposed in a construct, genome, chromosome, or episome. Thus, a promoter operably linked to a gene to which it is not operably linked to in its natural state (i.e. in the genome of a non-genetically engineered organism) is referred to herein as a "heterologous promoter," even though the promoter may be derived from the same species (or, in some cases, the same organism) as the gene to which it is linked.

As used herein, the term "protein" or "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" can be used instead of, or interchangeably with any of these terms.

Gene and protein Accession numbers, commonly provided in parentheses after a gene or species name, are unique identifiers for a sequence record publicly available at the National Center for Biotechnology Information (NCBI) website (ncbi.nlm.nih.gov) maintained by the United States National Institutes of Health. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appear in a specific GenBank record. Searching and obtaining nucleic acid or gene sequences or protein sequences based on Accession numbers and GI numbers is well known in the arts of, e.g., cell biology, biochemistry, molecular biology, and molecular genetics.

As used herein, the terms "percent identity" or "homology" with respect to nucleic acid or polypeptide sequences are defined as the percentage of nucleotide or amino acid residues in the candidate sequence that are identical with the known polypeptides, after aligning the sequences for maximum percent identity and introducing gaps, if necessary, to achieve the maximum percent homology. N-terminal or C-terminal insertion or deletions shall not be construed as affecting homology, and internal deletions and/or insertions into the polypeptide sequence of less than about 30, less than about 20, or less than about 10 amino acid residues shall not be construed as affecting homology. Homology or identity at the nucleotide or amino acid sequence level can be determined by BLAST (Basic Local Alignment Search Tool) analysis using the algorithm employed by the programs blastp, blastn, blastx, tblastn, and tblastx (Altschul (1997), *Nucleic Acids Res.* 25, 3389-3402, and Karlin (1990), *Proc. Natl. Acad. Sci. USA* 87, 2264-2268), which are tailored for sequence similarity searching. The approach used by the BLAST program is to first consider similar segments, with and without gaps, between a query sequence and a database sequence, then to evaluate the statistical significance of all matches that are identified, and finally to summarize only those matches which satisfy a preselected threshold of significance. For a discussion of basic issues in similarity searching of sequence databases, see Altschul (1994), *Nature Genetics* 6, 119-129. The search parameters for histogram, descriptions, alignments, expect (i.e., the statistical significance threshold for reporting matches against database sequences), cutoff, matrix, and filter (low complexity) can be at the default settings. The default scoring matrix used by blastp, blastx, tblastn, and tblastx is the BLOSUM62 matrix (Henikoff (1992), *Proc. Natl. Acad. Sci. USA* 89, 10915-10919), recommended for query sequences over 85 in length (nucleotide bases or amino acids).

For blastn, designed for comparing nucleotide sequences, the scoring matrix is set by the ratios of M (i.e., the reward score for a pair of matching residues) to N (i.e., the penalty score for mismatching residues), wherein the default values for M and N can be +5 and −4, respectively. Four blastn parameters can be adjusted as follows: Q=10 (gap creation penalty); R=10 (gap extension penalty); wink=1 (generates word hits at every winkth position along the query); and gapw=16 (sets the window width within which gapped alignments are generated). The equivalent Blastp parameter settings for comparison of amino acid sequences can be: Q=9; R=2; wink=1; and gapw=32. A Bestfit comparison between sequences, available in the GCG package version 10.0, can use DNA parameters GAP=50 (gap creation penalty) and LEN=3 (gap extension penalty), and the equivalent settings in protein comparisons can be GAP=8 and LEN=2.

Also disclosed are polypeptide or nucleic acid sequences of the present invention that are variants of any sequence disclosed herein (e.g. any of SEQ ID NO: 1-29), having sequence identities of at least 40%, at least 45%, at least 50%, at least 55%, of at least 70%, at least 65%, at least 70%, at least 75%, at least 80%, or at least 85%, for example at least 86%, at least 87%, at least 88%, at least 89%, at least 90%, at least 91%, at least 92%, at least 93%, at least 94%, at least 95%, at least 96%, at least 97%, at least 98%, at least 99%, or about 100% sequence identity with the full-length polypeptide or nucleic acid sequence, or to fragments thereof comprising a consecutive sequence of at least 50, or at least 100, at least 125, at least 150 or more amino acid residues of the entire protein or nucleotides of a nucleic acid sequence. Variants of disclosed sequences can have at least one amino acid residue or nucleotide has been inserted N- and/or C-terminal to, and/or within, the disclosed sequence(s) which contain(s) the insertion and substitution. Variants also include sequences having at least one substitution of an amino acid or nucleotide, e.g. in any of SEQ ID NO: 1-29, which can be a conservative amino acid substitution. Variants can also be nucleotide sequences that encode any amino acid sequence or variant thereof disclosed herein. Contemplated variants can additionally or alternatively include those containing predetermined mutations by, e.g., homologous recombination or site-directed or PCR mutagenesis, and the corresponding polypeptides or nucleic acids of other species, including, but not limited to, those described herein, the alleles or other naturally occurring variants of the family of polypeptides or nucleic acids which contain an insertion and substitution; and/or derivatives wherein the polypeptide has been covalently modified by substitution, chemical, enzymatic, or other appropriate means with a moiety other than a naturally occurring amino acid which contains the insertion and substitution (for example, a detectable moiety such as an enzyme). In any embodiment any of the disclosed polypeptide sequences can be an encoded methyltransferase in a mutant organism of the invention, or can be a nucleic acid sequence encoding such methyltransferase in the organism.

As used herein, the phrase "conservative amino acid substitution" or "conservative mutation" refers to the replacement of one amino acid by another amino acid with a common property. A functional way to define common properties between individual amino acids is to analyze the normalized frequencies of amino acid changes between corresponding proteins of homologous organisms (Schulz (1979) Principles of Protein Structure, Springer-Verlag). According to such analyses, groups of amino acids can be defined where amino acids within a group exchange preferentially with each other, and therefore resemble each other most in their impact on the overall protein structure (Schulz (1979) Principles of Protein Structure, Springer-Verlag). Examples of amino acid groups defined in this manner can include: a "charged/polar group" including Glu, Asp, Asn, Gln, Lys, Arg, and His; an "aromatic or cyclic group" including Pro, Phe, Tyr, and Trp; and an "aliphatic group" including Gly, Ala, Val, Leu, Ile, Met, Ser, Thr, and Cys. Within each group, subgroups can also be identified. For example, the group of charged/polar amino acids can be sub-divided into sub-groups including: the "positively-charged sub-group" comprising Lys, Arg and His; the "negatively-charged sub-group" comprising Glu and Asp; and the "polar sub-group" comprising Asn and Gln. In another example, the aromatic or cyclic group can be sub-divided into sub-groups including: the "nitrogen ring sub-group" comprising Pro, His, and Trp; and the "phenyl sub-group" comprising Phe and Tyr. In another further example, the aliphatic group can be sub-divided into sub-groups including: the "large aliphatic non-polar sub-group" comprising Val, Leu, and Ile; the "aliphatic slightly-polar sub-group" comprising Met, Ser, Thr, and Cys; and the "small-residue sub-group" comprising Gly and Ala. Examples of conservative mutations include amino acid substitutions of amino acids within the sub-groups above, such as, but not limited to: Lys for Arg or vice versa, such that a positive charge can be maintained; Glu for Asp or vice versa, such that a negative charge can be maintained; Ser for Thr or vice versa, such that a free —OH can be maintained; and Gln for Asn or vice versa, such that a free —NH2 can be maintained. A "conservative variant" is a polypeptide that includes one or more amino acids that have been substituted to replace one or more amino acids of the reference polypeptide (for example, a polypeptide whose sequence is disclosed in a publication or sequence database, or whose sequence has been determined by nucleic acid sequencing) with an amino acid having common properties, e.g., belonging to the same amino acid group or sub-group as delineated above.

As used herein, "expression" includes the expression of a gene at least at the level of RNA production, and an "expression product" includes the resultant product, e.g., a polypeptide or functional RNA (e.g., a ribosomal RNA, a tRNA, an antisense RNA, a micro RNA, a shRNA, a ribozyme, etc.), of an expressed gene. The term "increased expression" includes an alteration in gene expression to facilitate increased mRNA production and/or increased polypeptide expression. "Increased production" includes an increase in the amount of polypeptide expression, in the level of the enzymatic activity of a polypeptide, or a combination of both, as compared to the native production or enzymatic activity of the polypeptide.

Some aspects of the present invention include the partial, substantial, or complete attenuation, deletion, silencing, inactivation, or down-regulation of expression of particular polynucleotide sequences. The genes may be partially, substantially, or completely deleted, silenced, inactivated, or their expression may be down-regulated in order to affect the activity performed by the polypeptide they encode, such as the activity of an enzyme. Genes can be partially, substantially, or completely deleted, silenced, inactivated, or down-regulated by insertion of nucleic acid sequences that disrupt the function and/or expression of the gene (e.g., viral insertion, transposon mutagenesis, meganuclease engineering, homologous recombination, or other methods known in the art). The terms "eliminate," "elimination," and "knockout" can be used interchangeably with the terms "deletion," "partial deletion," "substantial deletion," or "complete deletion." In certain embodiments, a microorganism of interest may be engineered by site-directed homologous recombination or targeted integration or mutation using a Cas/CRISPR system to knockout a particular gene of interest. In still other embodiments, targeted insertion into or mutation of a gene regulatory region using a Cas/CRISPR system, RNAi, or antisense DNA (asDNA) constructs may be used to partially, substantially, or completely silence, inactivate, or down-regulate a particular gene of interest.

These insertions, deletions, or other modifications of certain nucleic acid molecules or particular polynucleotide sequences may be understood to encompass "genetic modification(s)" or "transformation(s)" such that the resulting strains of the microorganisms or host cells may be understood to be "genetically modified", "genetically engineered" or "transformed."

As used herein, "enhancing the expression" includes an increase in expression of a gene or nucleic acid molecule of interest or the activity of an enzyme in a photosynthetic organism comprising one or more genetic modifications as compared to the expression or activity in a control photosynthetic organism without such genetic modifications.

As used herein, "mutant" refers to an organism that has a mutation in a gene that is the result of classical mutagenesis, for example, using gamma irradiation, UV, or chemical mutagens. "Mutant" as used herein also refers to a recombinant cell that has altered structure or expression of a gene as a result of genetic engineering that may include, as non-limiting examples, overexpression, including expression of a gene under different temporal, biological, or environmental regulation and/or to a different degree than occurs naturally and/or expression of a gene that is not naturally expressed in the recombinant cell; homologous recombination, including knock-outs and knock-ins (for example, gene replacement with genes encoding polypeptides having greater or lesser activity than the wild-type polypeptide, and/or dominant negative polypeptides); gene attenuation via RNAi, antisense RNA, or ribozymes, or the like; and genome engineering using meganucleases, TALENs, and/or CRISPR technologies, and the like. A mutant is therefore not a naturally-occurring organism. A mutant organism of interest will typically have a phenotype different than that of the corresponding wild-type or progenitor strain that lacks the mutation, where the phenotype can be assessed by growth assays, product analysis, photosynthetic properties, biochemical assays, etc. When referring to a gene "mutant" means the gene has at least one base (nucleotide) change, deletion, or insertion with respect to a native or wild-type gene. The mutation (change, deletion, and/or insertion of one or more nucleotides) can be in the coding region of the gene or can be in an intron, 3' UTR, 5' UTR, or promoter region, e.g., within 2 kb of the transcriptional start site or within 3 kb or the translational start site. For example, a mutant having attenuated expression of a gene as disclosed herein can have a mutation, which can be one or more nucleobase changes and/or one or more nucleobase deletions and/or one or more nucleobase insertions, into the region of a gene 5' of the transcriptional start site, such as, in non-limiting examples, within 2 kb, within 1.5 kb, within 1 kb, or within 0.5 kb of the known or putative transcriptional start site, or within 3 kb, within 2.5 kb, within 2 kb, within 1.5 kb, within 1 kb, or within 0.5 kb of the translational start site. As nonlimiting examples, a mutant gene can be a gene that has a mutation, insertion, or deletion within the promoter region that can either increase or decrease expression of the gene; can be a gene that has a deletion that results in production of a nonfunctional protein, truncated protein, dominant negative protein, or no protein; can be a gene that has one or more point mutations leading to a change in the amino acid of the encoded protein or results in aberrant splicing of the gene transcript, etc.

Conserved domains of polypeptides include those identified in the "cd" (conserved domain) database, the COG database, the SMART database, the PRK database, the TIGRFAM database, or others known the art. The National Center for Biotechnology Information website provides a conserved domain database (CDD) which it describes as "a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM)." Any of these resources can be used to identify conserved domains.

The term "Pfam" refers to a large collection of protein domains and protein families maintained by the Pfam Consortium and available at several sponsored worldwide websites, including: Pfam.sanger.ac.uk/ (Welcome Trust, Sanger Institute); pfam.sbc.su.se (Stockholm Bioinformatics Center); pfam.janelia.org/ (Janelia Farm, Howard Hughes Medical Institute); pfam.jouy.inra.fr/ (Institut national de la Recherche Agronomique); and pfam.ccbb.re.kr. The latest release of Pfam is Pfam 32.0 (September 2018). Pfam domains and families are identified using multiple sequence alignments and hidden Markov models (HMMs). Pfam-A family or domain assignments, are high-quality assignments generated by a curated seed alignment using representative members of a protein family and profile hidden Markov models based on the seed alignment. (Unless otherwise specified, matches of a queried protein to a Pfam domain or family are Pfam-A matches.) All identified sequences belonging to the family are then used to automatically generate a full alignment for the family (Sonnhammer (1998) *Nucleic Acids Research* 26, 320-322; Bateman (2000) Nucleic Acids Research 26, 263-266; Bateman (2004) *Nucleic Acids Research* 32, Database Issue, D138-D141; Finn (2006) *Nucleic Acids Research* Database Issue 34, D247-251; Finn (2010) *Nucleic Acids Research* Database Issue 38, D211-222). By accessing the Pfam database, for example, using any of the above-referenced websites, protein sequences can be queried against the HMMs using HMMER homology search software (e.g., HMMER2, HMMER3, or a higher version, hmmer.janelia.org/). Significant matches that identify a queried protein as being in a Pfam family (or as having a particular Pfam domain) are those in which the bit score is greater than or equal to the gathering threshold for the Pfam domain. Expectation values (e values) can also be used as a criterion for inclusion of a queried protein in a Pfam or for determining whether a queried protein has a particular Pfam domain, where low e values (much less than 1.0, for example less than 0.1, or less than or equal to 0.01) represent low probabilities that a match is due to chance.

Reference to properties that are "substantially the same" or "substantially identical" indicates minor and irrelevant deviations that are not material to the characteristics considered important in the context of the invention. In various embodiments this can mean the properties are within 10%, and preferably within 5%, or within 2.5%, of the reference value.

A "control cell" or "control microorganism" is either a wild-type cell or microorganism from which the mutant microorganism (genetically engineered or mutagenized microorganism) is directly or indirectly derived, or is a cell or microorganism that is substantially identical to the mutant cell or microorganism referred to, with the exception that the control cell or microorganism does not have the mutation resulting in increased lipid production, for example, the control cell or microorganism has not been genetically engineered or mutagenized to increase lipid production. For example, where the recombinant alga comprises an exogenous gene encoding a Cas9 gene and knockout of the indigenous CHG methyltransferase gene, a control alga can be substantially identical to the recombinant alga with the exception that the control alga does not comprise a knockout of the CHG methyltransferase gene.

Disclosed herein are methods for manipulating, assaying, culturing, and analyzing microorganisms. The invention set forth herein also makes use of standard methods, techniques, and reagents for cell culture, the transformation of microorganisms, genetic engineering, and biochemical analysis that are known in the art. Although methods and materials similar or equivalent to those described herein can be used in practice or testing of the present invention, suitable methods and materials are described below. The materials, methods, and examples are illustrative only and are not intended to be limiting. Other features and advantages of the invention will be apparent from the description and from the claims.

EXAMPLES

Example 1

Development of a Fully Penetrant Cas9-Expressing Parachlorella Strain

Parachlorella strain was genetically engineered to express *Streptococcus pyogenes* Cas9 gene using a method essentially as described in PCT application publication WO2016109840, which is incorporated by reference in its entirety. Briefly, *Parachlorella* strain WT-1185 was transformed with a vector comprising *Streptococcus pyogenes* Cas9 gene operably linked to the *Parachlorella* RPS17 promoter, blasticidin resistance gene from *Aspergillus terreus* codon optimized for *Parachlorella*, a GFP reporter expression cassette operably linked to the *Parachlorella* ACP1 promoter to generate *Parachlorella* strain STR00014. The integration of the Cas9 gene and the GFP genes into the *Parachlorella* genome were confirmed by sequencing, a shift in fluorescence by flow cytometry and the demonstration of Cas9 protein expression by Western blotting.

Example 2

Identification of *Parachlorella* DNA Methyltransferases

Four novel putative DNA methyltransferase genes comprising Pfam PF00145 (C-5 cytosine-specific DNA methyltransferase) in *Parachlorella* sp. were identified from a sequence database using Pfam analysis, BLAST search, and HMMER. Each of these 4 putative methyltransferase genes comprises Pfam PF00145 that corresponds to C-5 cytosine-specific DNA methyltransferase. The amino acid sequences and their corresponding cDNA sequences of *Parachlorella* putative DNA methyltransferases were shown as SEQ ID NO: 1-8.

Example 3

Knockout of Each of the Four Putative DNA Methyltransferase Using Fully Penetrant *Parachlorella* Cas9 Editor Strain Str00014

Each of the individual putative DNA methyltransferase were knocked out using the CRISPR Cas9 integrated into the *Parachlorella* Cas9 editor background strain STR00014 (which is a wild-type strain having a Cas9 cassette) and a chimeric gRNAs for each of the genes. Chimeric gRNA was designed and synthesized in vitro to target four DNA methyltransferase genes in *Parachlorella*: EMRE3EUKT598198, EMRE3EUKT590754, EMRE3EUKT596408, and EMRE3EUKT596208—their respective chimeric gRNA sequences are shown as SEQ ID Nos: 9-12.

*Parachlorella* STR00014 was transformed by electroporation with 1-2 µg of purified chimeric guide RNA, and 1 µg of selectable marker DNA which contained a bleomycin resistance "BleR" gene codon-optimized for *Parachlorella* and containing introns from *Parachlorella* (SEQ ID: 13). The BleR gene was operably linked to the *Parachlorella* RPS4 promoter (SEQ ID: 14) and terminated by the *Parachlorella* RPS4 terminator (SEQ ID: 15).

Electroporation was performed by inoculating a 100 mL seed culture inoculated to $1\times10^6$ cells/mL six days before transformation was used to inoculate a 1 L culture to $1\times10^6$ cells/mL two days before transformation. On the day of transformation, cells were pelleted by centrifugation at 5000×g for 20 minutes, washed three times with 0.1 um filtered 385 mM sorbitol, and resuspended to $5\times10^9$ cells/mL in 385 mM sorbitol. Electroporation of 100 µL concentrated cells was performed in 0.2 cm cuvettes in a Bio-Rad® Gene Pulser Xcell™ under varied conditions. The DNA used for optimization of electroporation was linearized pSG6640 including the ble and TurboGFP expression cassettes. The TurboGFP cassette included the *Parachlorella* ACP promoter (SEQ ID NO:16) operably linked to the TurboGFP gene (SEQ ID NO:17) and the *Parachlorella* ACP terminator (SEQ ID NO:18) Immediately after electroporating pre-chilled cells and cuvettes, 1 mL cold sorbitol was added and used to transfer cells into 10 mL of commercially available algal growth medium. After overnight recovery, cells were concentrated and spread onto 13 cm-diameter of the growth media containing zeocin at 250 mg/L and grown under the conditions listed in the biolistics section. The sequences of the *Parachlorella* ACP promoter, ACP terminator, and the TurboGFP gene are shown below.

After testing a range of voltages, resistances, and capacitances, the optimal electroporation conditions were determined to be 1.0-1.2 kV (5000-6000 V/cm), 200-300 ohms, and 25-50 µF. Use of larger quantities of DNA increased the resulting number of zeocin-resistant colonies, though the effect plateaued at amounts larger than 4 µg.

Following electroporation, cells were plated on agar medium (a commercially available algal growth medium supplemented with 10 mM ammonium and 15 mM HEPES pH 8) containing 250 µg/ml zeocin to select for transformants that incorporated the bleR cassette. Transformants for EMRE3EUKT598198 knockouts were screened by colony PCR using primers designed to amplify across the native targeted locus (DNA_oligoST106; SEQ ID: 19, and DNA_oligoST107; SEQ ID: 20). The primers were designed to produce a ~400 bp band in the absence of integration (e.g., "knock-in" of the BleR cassette) into the locus, or a ~5.1 kb band if there was integration of a single BleR cassette into the targeted locus, or possibly no band if there are multiple integrations into the targeted locus. In addition, two more colony PCR reactions were done using each one of the primers described above flanking the target, and an internal BleR primer (DNA_oligoST078; SEQ ID: 21), designed to amplify from the chromosome into the selectable marker. Regardless of the orientation of the integrated ble cassette, a ~800 bp band would result from amplification by either flanking primer and internal primer DNA_oligoST078 if targeted integration was successful. The sequences of the primers are shown below.

```
DNA_oligoST106
                                      (SEQ ID NO: 19)
gtgtgggtgctctggatcagccatcgat DNA_oligoST107
                                      (SEQ ID NO: 20)
tgagaaagcaagctgtgcaggagctcagg DNA_oligoST078
                                      (SEQ ID NO: 21)
GCGTGCACTTTGTTGCAGAAGAACAGGACTG
```

The resulting EMRE3EUKT598198 knockout strain is termed STR03778.

Transformants for EMRE3EUKT590754 knockouts were screened by colony PCR using primers designed to amplify across the native targeted locus (DNA_oligoST258; SEQ ID: 22, and DNA_oligoST259; SEQ ID: 23). The primers were designed to produce a ~400 bp band in the absence of integration (e.g., "knock-in" of the BleR cassette) into the locus, or a ~5.1 kb band if there was integration of a single BleR cassette into the targeted locus, or possibly no band if there are multiple integrations into the targeted locus. In addition, two more colony PCR reactions were done using each one of the primers described above flanking the target, and an internal BleR primer (SEQ ID: 21), designed to amplify from the chromosome into the selectable marker. Regardless of the orientation of the integrated ble cassette, a ~800 bp band would result from amplification by either flanking primer and internal primer DNA_oligoST078 if targeted integration was successful. The sequences of the primers are shown below.

```
DNA_oligoST258
                                        (SEQ ID NO: 22)
gtgtcatcttcagtgccaccctctttccgc DNA_oligoST259
                                        (SEQ ID NO: 23)
ctagcagcagcagcctcaatatgctgctgc
```

The resulting EMRE3EUKT590754 knockout strain is termed STR03826.

Transformants for EMRE3EUKT596408 knockouts were screened by colony PCR using primers designed to amplify across the native targeted locus (DNA_oligoST108; SEQ ID: 24, and DNA_oligoST109; SEQ ID: 25). The primers were designed to produce a ~400 bp band in the absence of integration (e.g., "knock-in" of the BleR cassette) into the locus, or a ~5.1 kb band if there was integration of a single BleR cassette into the targeted locus, or possibly no band if there are multiple integrations into the targeted locus. In addition, two more colony PCR reactions were done using each one of the primers described above flanking the target, and an internal BleR primer (DNA_oligoST078; SEQ ID: DNA_oligoST078), designed to amplify from the chromosome into the selectable marker. Regardless of the orientation of the integrated ble cassette, a ~800 bp band would result from amplification by either flanking primer and internal primer DNA_oligoST078 if targeted integration was successful.

```
DNA_oligoST108
                                        (SEQ ID NO: 24)
cagaattcttagctgtgccccagtgcatgg DNA_oligoST109
                                        (SEQ ID NO: 25)
ctccaagcttgatcacagctcgccacatc
```

The resulting EMRE3EUKT596408 knockout strain is termed STR03749.

Transformants for EMRE3EUKT596208 knockouts were screened by colony PCR using primers designed to amplify across the native targeted locus (DNA_oligoST110; SEQ ID: 26, and DNA_oligoST111; SEQ ID: 27). The primers were designed to produce a ~400 bp band in the absence of integration (e.g., "knock-in" of the BleR cassette) into the locus, or a ~5.1 kb band if there was integration of a single BleR cassette into the targeted locus, or possibly no band if there are multiple integrations into the targeted locus. In addition, two more colony PCR reactions were done using each one of the primers described above flanking the target, and an internal BleR primer (DNA_oligoST078; SEQ ID: DNA_oligoST078), designed to amplify from the chromosome into the selectable marker. Regardless of the orientation of the integrated ble cassette, a ~800 bp band would result from amplification by either flanking primer and internal primer DNA_oligoST078 if targeted integration was successful. The sequences of the primers are shown below.

```
DNA_oligoST110
                                        (SEQ ID NO: 26)
gccgcgcacttcacctgtacagaccgt DNA_oligoST111
                                        (SEQ ID NO: 27)
ctgcaggacagcagttgctgaacttgcc
```

The resulting EMRE3EUKT596208 knockout strain is termed STR03779.

The *Parachlorella* DNA methyltransferase genes, SEQ ID NOs for the amino acid and DNA sequences, the corresponding gRNA sequences used for knockout of these genes, and the corresponding knockout strains are summarized below.

TABLE 1

*Parachlorella* DNA methyltransferases and corresponding sequences

| Internal Gene ID | SEQ ID NO for amino acid sequence | SEQ ID NO for cDNA sequence | SEQ ID NO for the corresponding gRNA sequence used for knockout | Strain |
|---|---|---|---|---|
| EMRE3EUKT598198 | 1 | 2 | 9 | STR03778 |
| EMRE3EUKT590754 | 3 | 4 | 10 | STR03826 |
| EMRE3EUKT596408 | 5 | 6 | 11 | STR03749 |
| EMRE3EUKT596208 | 7 | 8 | 12 | STR03779 |

Example 4

Analysis of the Knockout Strains for DNA Methyltransferase Activities

DNA Methylation Status

The CpG, CHG, and CHH cystine methylation status of the *Parachlorella* native DNA as well as of the exogenous DNA that are integrated into the *Parachlorella* sp. genome (e.g., Blasticidin, Cas-9, and GFP DNA sequences) were evaluated for the *Parachlorella* DNA methyltransferase knockout strains STR03749, STR03826, STR03779, and STR03778 and compared with the control *Parachlorella* strain STR00014 comprising Blasticidin, Cas9, and GFP genes integrated into its genome and intact DNA methyltransferases.

Briefly, *Parachlorella* chromosomal DNA was isolated using the standard techniques. Methylation status of the isolated DNA was analyzed using MethylSeg™ (Illumina Inc., San Diego, Calif.).

*Parachlorella* Knockout Strain STR03778

The level of CHG DNA methylation of the exogenous genes Blasticidin, Cas-9, and GFP integrated into the Parachlorella sp. genome were significantly reduced in the Parachlorella DNA methyltransferase knockout strain STR03778 as compared to the control Parachlorella strain STR00014 without such knockout (FIG. 1).

Additionally, the level of CHH DNA methylation of the exogenous genes Blasticidin, Cas-9, and GFP integrated into the Parachlorella sp. genome were reduced in the Parachlorella DNA methyltransferase knockout strain STR03778 as compared to the control Parachlorella strain STR00014 without such knockout (FIG. 1). However, the level of CpG DNA methylation of the exogenous genes Blasticidin, Cas-9, and GFP integrated into the Parachlorella sp. genome remained relatively unchanged for Parachlorella DNA methyltransferase knockout strain STR03778 as compared to the control Parachlorella strain STR00014 without such knockout (FIG. 1).

Figure 2:
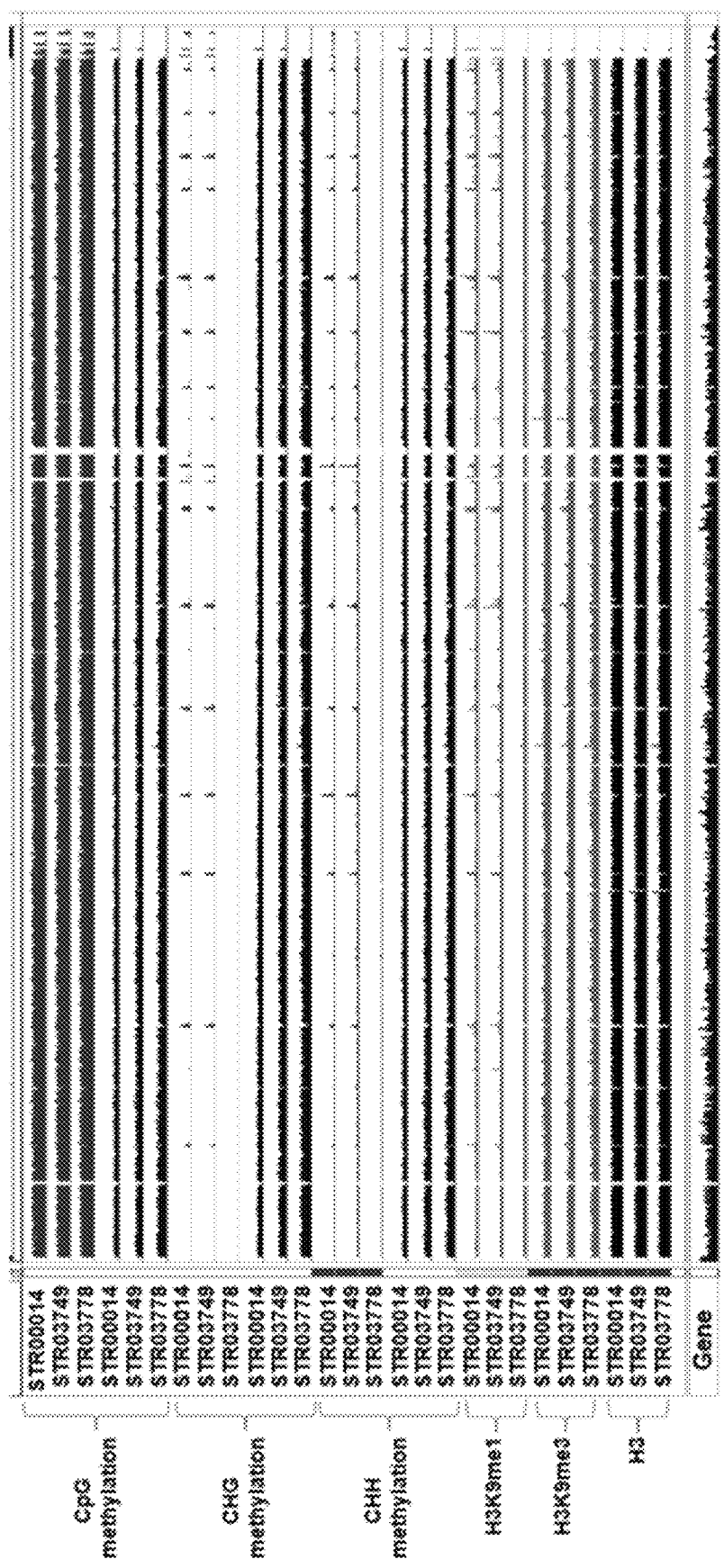
FIG. 2 shows the general absence of CHG, and CHH DNA methylation and mono and trimethylation of H3K9, other than at repetitive and centromeric regions of the native *Parachlorella* DNA. The native DNA methylation and H3K9 monomethylation and trimethylation status of the *Parachlorella* knockout strains STR03778 and STR03749 were compared with the *Parachlorella* control strain STR00014 (see Table 1 for additional info). Representative native DNA genome tracks depicting the percent DNA methylation (first set of rows) and the genome coverage (second set of rows) were shown, as well as the sequence information from ChIPs with 3 *Parachlorella* strains isolated with antibodies specific for H3K9me1 and H3K9me3. Tracks are scaled to allow comparison across different samples. The coverage tracks for histone 3 (H3) are also shown. The chromosome position is shown at the top, and the gene models are provided at the bottom.
Figure 3:
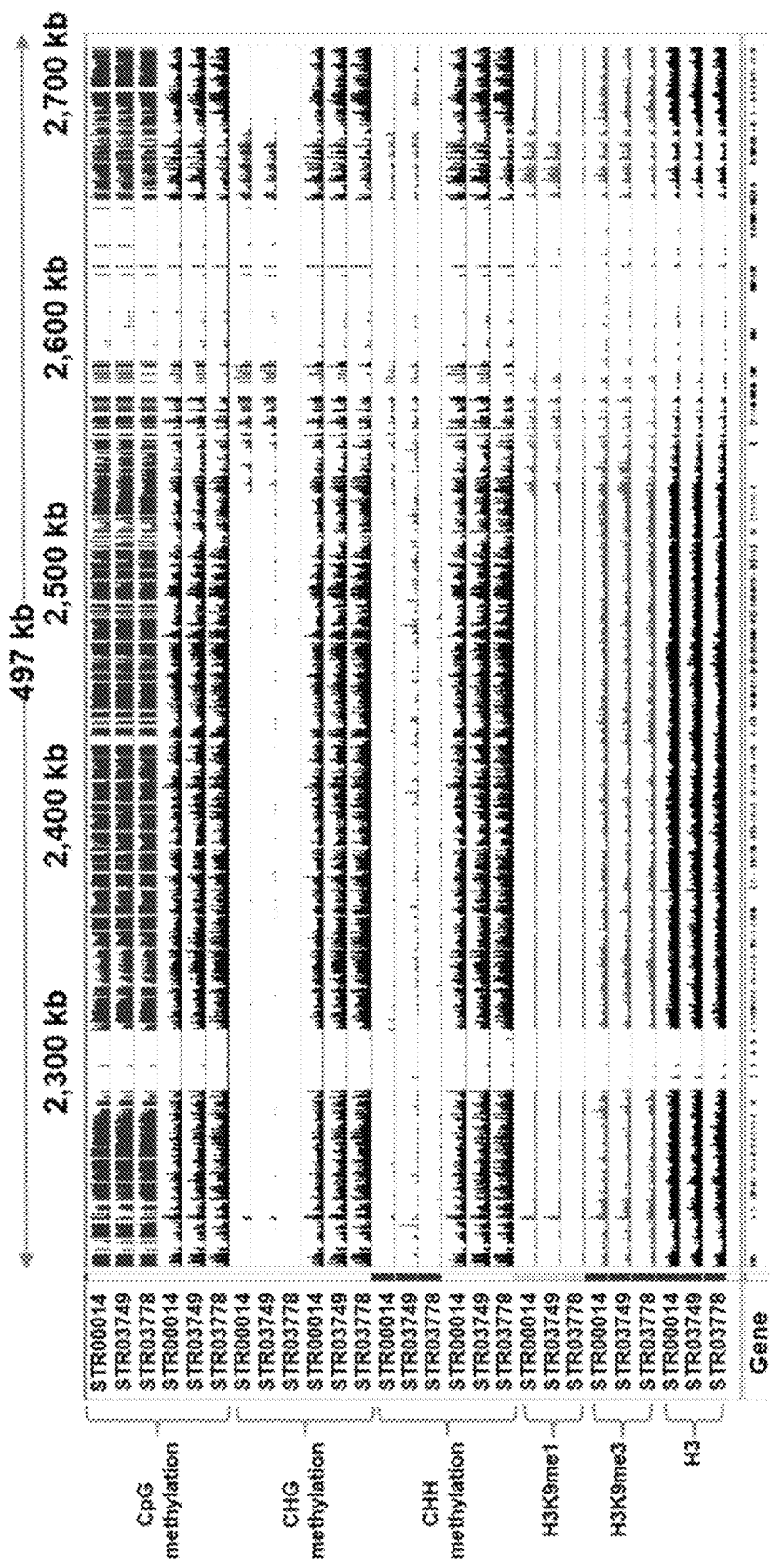
FIG. 3 shows the general absence of CHG, and CHH DNA methylation and mono and trimethylation of H3K9, other than at repetitive regions, transposable elements, and centromeric regions of chromosome 2 of the native *Parachlorella* DNA. The DNA methylation and H3K9 monomethylation and trimethylation status of the *Parachlorella* knockout strains STR03778 and STR03749 were compared with the *Parachlorella* control strain STR00014. Representative native DNA genome tracks depicting the percent DNA methylation (first set of rows) and the genome coverage (second set of rows) are shown, as well as the sequencing reads from ChIPs with 3 *Parachlorella* strains pulled down with antibodies specific for H3K9me1 and H3K9me3. Tracks are scaled to allow comparison across different samples. The coverage tracks for histone 3 (H3) are also shown. The chromosome position is shown at the top, and the gene models are provided at the bottom.

The level of CHG, CHH, and CpG DNA methylation of native Parachlorella DNA sequences were also evaluated. The Parachlorella DNA methyltransferase knockout strain STR03778 exhibited lower CHG methylation at the highly repetitive sequences and at the centromere regions of its genome as compared to the control Parachlorella strain STR00014 without such knockout but the level of CHH, and CpG DNA methylation of native Parachlorella DNA sequences remained relatively unchanged (FIGS. 2 and 3).

Parachlorella Knockout Strain STR03749

The level of CHG, CpG, and CHH DNA methylation of the exogenous genes Blasticidin, Cas-9, and GFP integrated into the Parachlorella sp. genome remained relatively unchanged for Parachlorella DNA methyltransferase knockout strain STR03749 as compared to the control Parachlorella strain STR00014 without such knockout (FIG. 1).

The level of CHG, CHH, and CpG DNA methylation of native Parachlorella DNA sequences were also evaluated. The level of CHG, CHH, and CpG DNA methylation of native Parachlorella DNA sequences remained relatively unchanged (FIGS. 2 and 3).

Parachlorella Knockout Strains STR03826 and STR03779

Parachlorella knockout strains STR03826, STR03779 showed similar methylation patterns as the Parachlorella knockout strain STR03749 (data not shown).

Thus, Parachlorella gene EMRE3EUKT598198 is responsible for methylation of exogenous DNA.

Example 5

Analysis of the Knockout Strains for H3K9 Mono- and Trimethylation

The monomethylation and trimethylation of lysine 9 of histone 3 (H3K9) were evaluated for control Parachlorella strain STR00014 and DNA methyltransferase knockout strains STR03749 and STR03778 using chromatin immunoprecipitation techniques (ChIP) using the reagents from Active Motif® (Carlsbad, Calif., Catalog No. 53040). Antibodies specific for trimethylated lysine 9 of histone 3 were purchased from Abcam® (Cambridge, Mass.) and used for the ChIP assay.

Parachlorella DNA methyltransferase knockout strain STR03778 (knockout of EMRE3EUKT598198 gene, encoding SEQ ID NO: 1) showed a significant reduction of H3K9 monomethylation and trimethylation in the chromosome portions comprising exogenous genes blasticidin, Cas-9, and GFP integrated into the Parachlorella genome as compared to control Parachlorella strain STR00014 without such knockout (FIG. 1).

Parachlorella DNA methyltransferase knockout strain STR03778 (knockout of EMRE3EUKT598198 gene) showed a slight reduction of H3K9 monomethylation and trimethylation in the native chromosome (FIGS. 2 and 3).

Parachlorella strain STR03749 showed no significant change in the mono- and trimethylation of H3K9 (FIGS. 1-3). Thus, Parachlorella gene EMRE3EUKT598198 is indirectly involved in the mono and trimethylation of histone H3K9 of integrated exogenous DNA.

Figure 9:
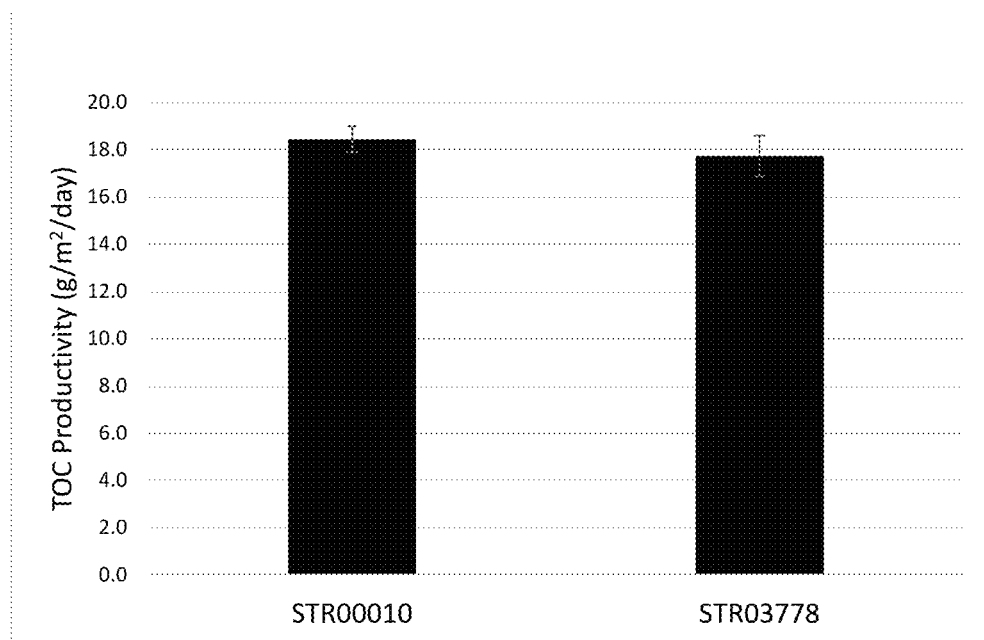
FIG. 9 shows the results of a productivity assay in *Parachlorella* sp. (STR03778 with deletion of the methyltransferase of SEQ ID NO: 2) measured as total organic carbon (TOC) as an indicator of productivity under semi-continuous areal culture. The data show no defects in productivity for the cell compared to a wild-type *Parachlorella* sp. strain (STR0010).

FIG. 9 also shows the results of productivity (as total organic carbon) for the knockout strain. The results show no defects in productivity compared to a wild-type strain.

Example 6

Evaluation of the Protein Expression of the Exogenous Genes

Expression of exogenous gene Cas-9 integrated into the Parachlorella genome was evaluated by Western blot analysis for three knockout strains STR03778, STR03749, and STR03779 and compared with the control strain STR00014. The anti-Cas-9 antibody was used for the Western blot analysis.

Figure 4:
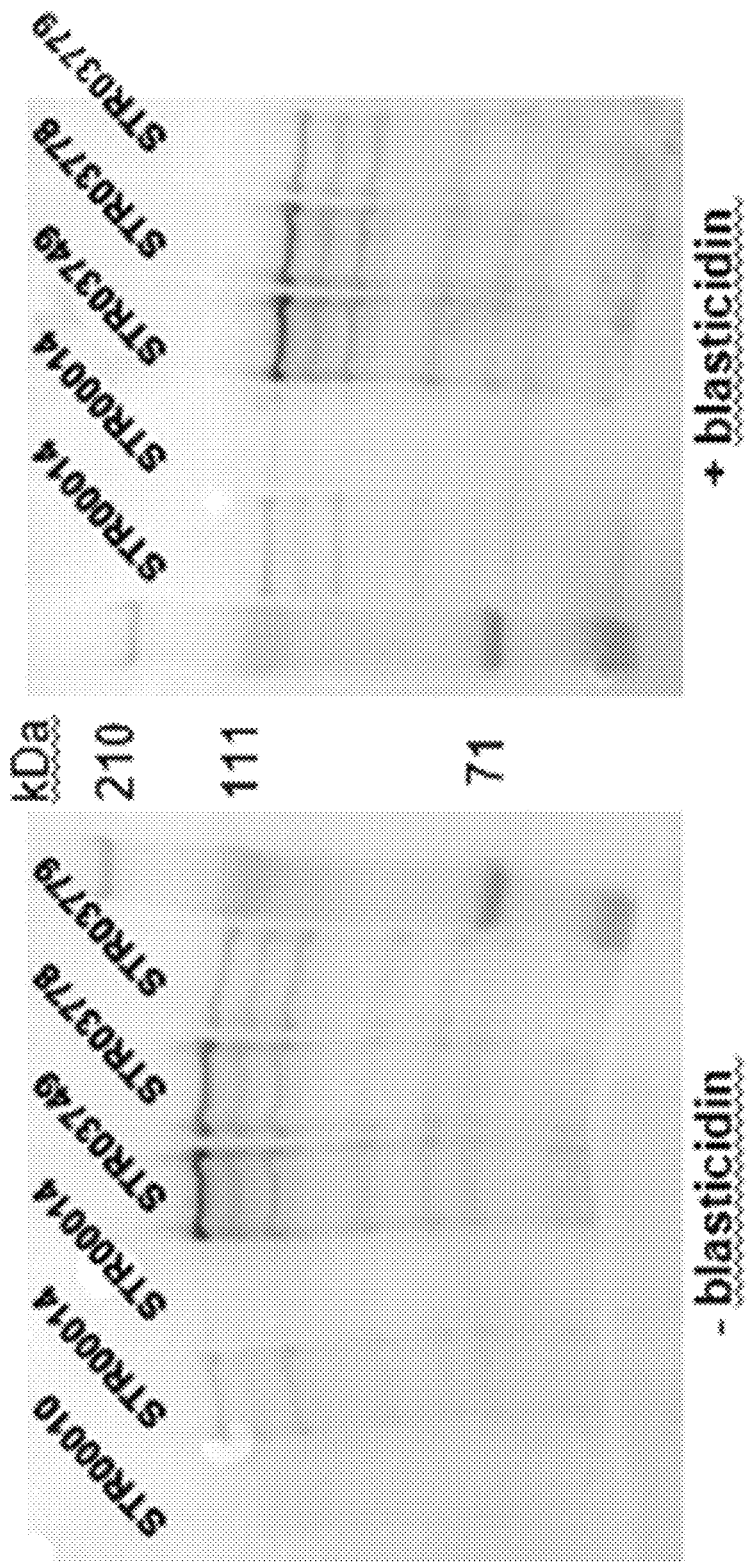
FIG. 4 shows a comparison of the exogenous gene expression in selected *Parachlorella* knockout strains STR03749, STR03778, STR03779 as compared to the *Parachlorella* control strain STR00014 as measured by Western blotting.

The level of expression of the Cas-9 protein was higher in both the knockout strains STR03778 and STR03749 as compared to the control strain STR00014 in the presence or absence of a selective pressure of blasticidin (FIG. 4).

Thus, mutating or attenuating the Parachlorella gene EMRE3EUKT598198 increases the expression of exogenous DNA in Parachlorella sp.

Example 7

Identification of Orthologous DNA Methyltransferase in Other Algal Species

The amino acid sequence of Parachlorella gene EMRE3EUKT598198 (SEQ ID NO: 1) was used to identify orthologous DNA methyltransferases in the alga Oocystis sp. using BLAST analysis. The amino acid and cDNA sequences of the identified DNA methyltransferase is shown as SEQ ID Nos: 28-29.

Figure 5:
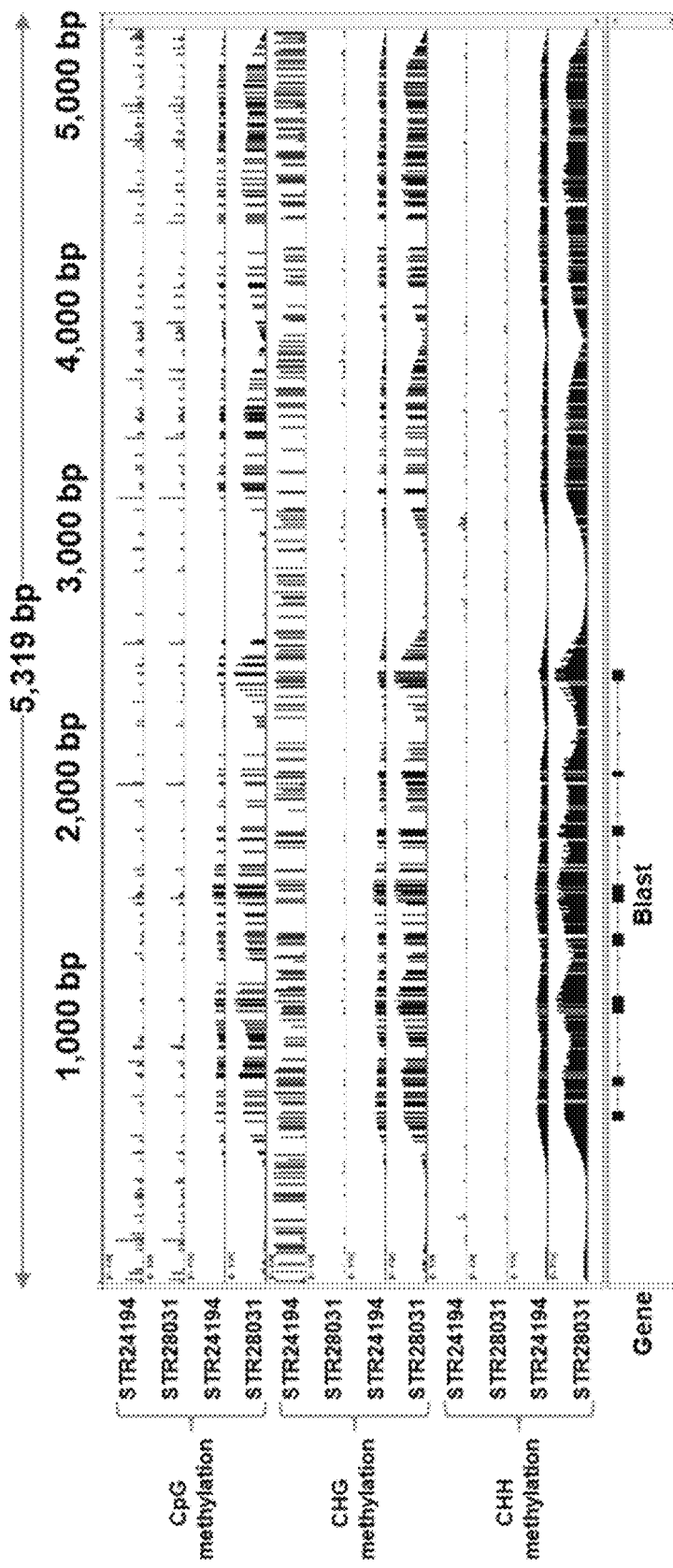
FIG. 5 shows a genome track illustrating the presence of DNA methylation (CpG, CHG, and CHH) of exogenous DNA (blasticidin gene) integrated into the *Oocystis* genome for the indicated strains. The first set of rows shows the percent of DNA methylation and the second set of rows the genome coverage. STR24194 is background strain and STR28031 is a knockout strain of SEQ ID NO: 29 (encoding SEQ ID NO: 28) and having blasticidin as selectable marker.
Figure 6:
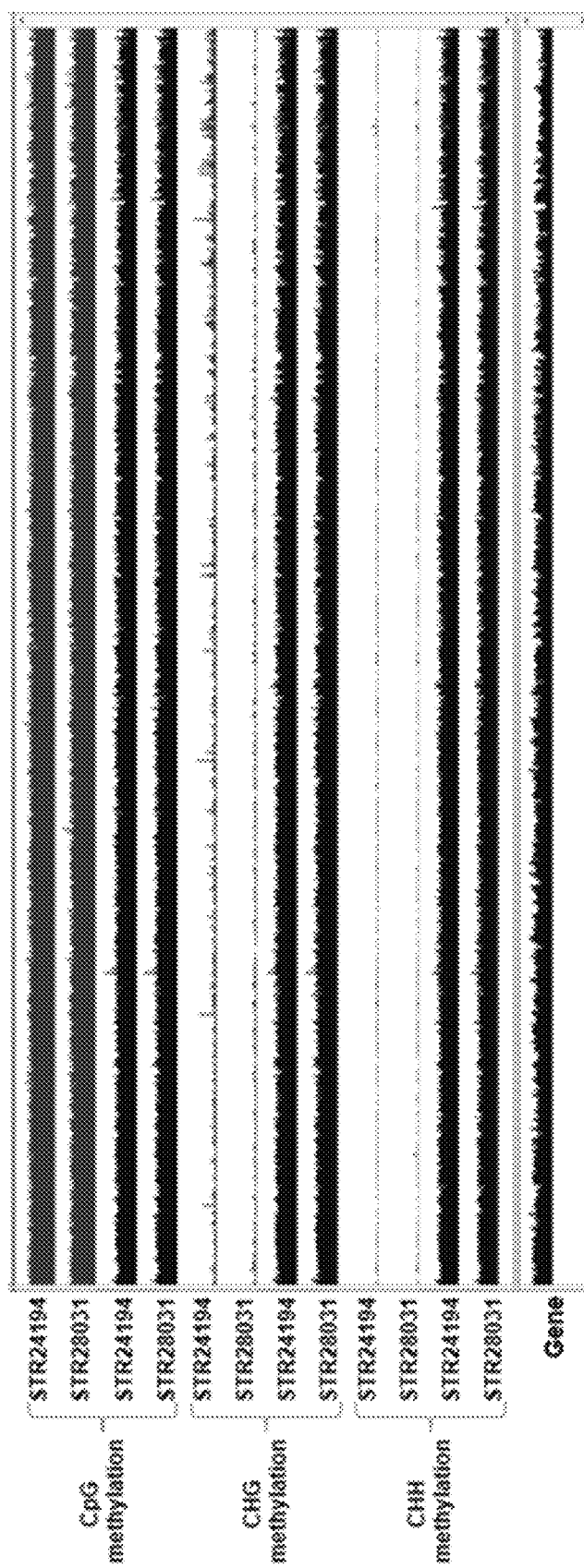
FIG. 6 shows a zoomed in genome track distribution of DNA methylation (CpG, CHG, and CHH) of the DNA in the background strain (STR24194) of the *Oocystis* genome. DNA depicting the percent DNA methylation (first set of rows) and the genome coverage (second set of rows) are shown.
Figure 7:
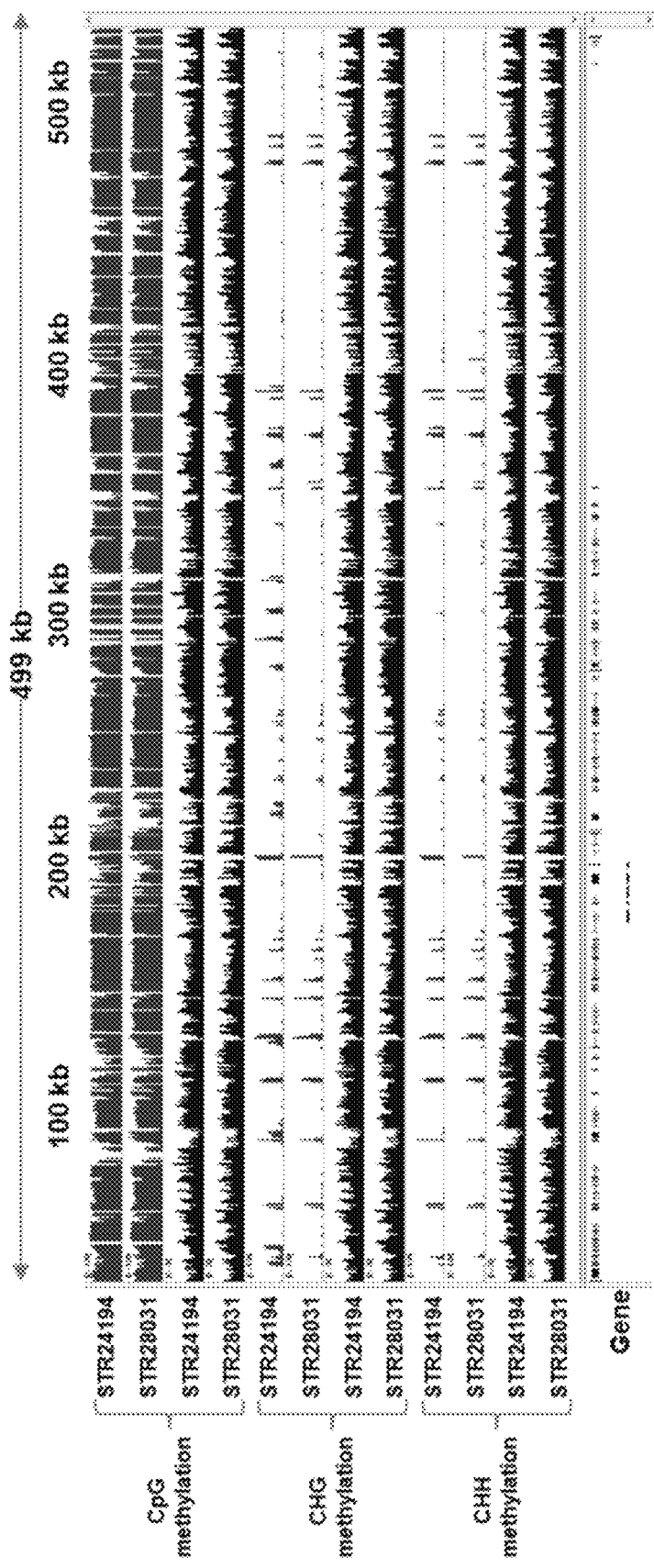
FIG. 7 shows a zoomed in genome track distribution of DNA methylation (CpG, CHG, CHH) of the native DNA of the *Oocystis* genome. DNA depicting the percent DNA methylation (first set of rows) and the genome coverage (second set of rows) are shown. STR28031 is a knockout strain of SEQ ID NO: 29 (encoding SEQ ID NO: 28) and having blasticidin as selectable marker; STR24194 is the background strain.

CHG DNA methylation of exogenous DNA (blasticidin gene) integrated into the Oocystis sp. genome, in addition to some CpG and CHH DNA methylations, was identified (FIGS. 5-7). In addition, the application identifies CHG methylation of Oocystis sp. DNA at the repetitive regions and at the centromere (FIGS. 6-7).

Example 8

Attenuation of CHG Methyltransferases in Oocystis

Methyltransferase genes were identified in Oocystis sp. as described above. The deletion of the sequence encoding the methyltransferase SEQ ID NO: 28 was generated with RNP/DNA coated bullets using a Helios® Gene Gun System (Bio-Rad, Hercules, Calif., USA). Selectable marker DNA and Cas9 ribonucleoprotein (RNP) targeting the gene to be knocked out were precipitated onto gold particles, the gold particles were adhered to the inside of tubing, and a burst of helium gas fired through the tubing by the gene gun thus projecting the coated gold particles into the Oocystis sp. cells adhered on solid non-selective media. The following day, the cells were moved to selective media for growth of transformed colonies.

Cas9 RNP was prepared using the Alt-R CRISPR-Cas9 system (Integrated DNA Technologies, Inc., Coralville, Iowa, USA). crRNA XT targeting the gene of interest was annealed to tracrRNA, and the resulting guide RNA duplex was complexed with Cas9 V3 to form the Cas9 RNP. The selectable marker DNA was prepped from *E. coli* and restriction digested to separate the backbone. Either NAS16305 (a vector encoding blasticidin-resistance) or NAS15142 (a vector encoding nourseothricin resistance) were used. Both markers were codon-optimized for *Oocystis* sp., contain endogenous introns from *Oocystis* sp., and operably linked to endogenous *Oocystis* sp. promoters and terminated by endogenous *Oocystis* sp. terminators.

0.6 um gold particles were resuspended in a protamine sulfate salt solution and sonicated. DNA marker was mixed with Cas9 RNP (62 pmol Cas9 V3 and 500 pmol guide RNA duplex) in PBS, and the DNA-RNP mixture was added to the protamine-gold solution to precipitate on ice for 2 hours.

A 7" length of Tefzel™ (ethylene tetrafluoroethylene) (E.I. du Pont de Nemours, Wilmington, Del.) tubing for each sample was inserted into the flexible tubing attached to a manifold drier (e.g. as described in published U.S. patent application US 2017-0130238). The flexible tubing was disconnected from the manifold drier at the Leur lock and attached to a 10 mL syringe. The DNA-RNP/gold suspension was mixed well and drawn into the Tefzel™ tubing by application of suction by the syringe. While still connected to the syringe, the Tefzel™ tubing was laid on a flat surface for two minutes while the gold settled out of solution and adhered to the inside of the tubing. Pressure was then applied with the syringe to gently push the PBS solution out of the tubing. The tubing was immediately turned over to allow the remaining gold slurry to smear to the side of the Tefzel™ tubing opposite where it originally settled. The Tefzel™ tubing was then detached from the syringe and moved back onto the manifold drier with 0.5-0.6 LPM nitrogen flowing. When the gold was completely dried as evidenced from a visible color change from dark to light yellow, the Tefzel™ tubing was removed from the flexible tubing and cut into half-inch pieces for use in the Helios Gene Gun™.

Transformation

To prepare cells for transformation, a 100 mL seed culture inoculated to 0.05 OD730 six days before transformation was used to inoculate a 500 mL culture to 0.2 OD730 one day before transformation. Cultures were grown in commercially available algal growth medium having a half concentration of salt in a plant growth chamber at 25° C. 1% CO2 shaking at 130 rpm in a 16:8 light:dark cycle.

On the day of transformation, cell cultures were pelleted by centrifugation at 5000×g for twenty minutes. Cells were resuspended in 50 mL osmoticum (250 mM mannitol/250 mM sorbitol 0.1 um filter-sterilized) and incubated for 1-2 hours at room temperature. After osmotic pre-treatment, cells were concentrated to 20.0 OD730/mL in osmoticum, and 200 uL of cell suspension was painted in each of five 4 cm-diameter circles on a 13 cm-diameter shooting plate containing 2% agar PM147 solid medium. When the cells were completely dried, the gene gun was used to fire two bullets per cell circle at 400 psi from a distance of 3-6 cm from the plate. In total for each sample, 10 replicate bullets were fired at 20.0 OD730 of cells, divided among 5 cell circles. Cells were left on the shooting plates overnight in a dark 30° C. incubator.

The day after transformation, cells from replicate cell circles were pooled together by washing the shooting plates with liquid commercially available algal growth medium. Recovered cells were plated onto the growth medium containing either 425 mg/L blasticidin or 80 mg/L nourseothricin sulfate) at an intended density of 10.0 OD730 per 13 cm-diameter plate.

Transformation of MTase Knockout Strain and Parental Strain with DNA Coated Bullets The *Oocystis* sp. methyltransferase (MT) knockout strain and parental strain were transformed with DNA using the Helios® Gene Gun System (Bio-Rad, Hercules, Calif., USA). DNA was precipitated onto gold particles, the gold particles were adhered to the inside of lengths of tubing, and a burst of helium gas fired through the tubing by the gene gun projected the DNA-coated gold particles into *Oocystis* sp. cells adhered on solid non-selective media. The following day, cells were moved onto selective media for growth of transformed colonies.

Figures 8A, 8B:
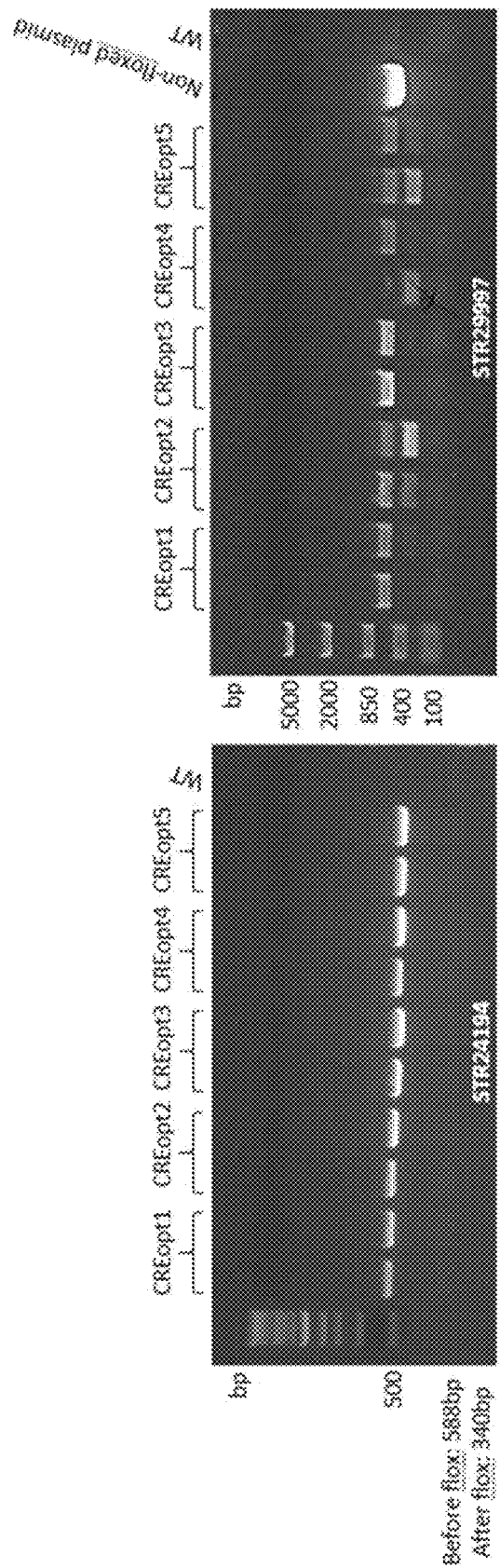
FIGS. 8A and 8B show agarose gels illustrating expression of the transgenes (Cre recombinase and Ble) in *Oocystis* sp.

Five DNA vectors (CRE1-5) encoding the same BSD selectable marker, but different versions of CRE recombinase were tested (FIG. 8). The different versions of CRE shared the same CDS sequence codon-optimized for *Oocystis* sp., yet each contained different endogenous introns from *Oocystis* sp. All CRE versions were operably linked to the same endogenous *Oocystis* sp. promoters and terminated by the same endogenous *Oocystis* sp. terminators. The vector DNA was prepped from *E. coli* and restriction digested to separate the backbone prior to transformation. The data show partial or complete floxing in the knockout strains. CHG methylation was extensive for the parental strains and absent in the knockout, as shown in FIGS. 5-7.

DNA (2-10 μg) was precipitated onto gold particles and resuspended in 100% ethanol solution. The volumes were calculated to make ten bullets, no PVP was used, and a protamine sulfate salt solution was used. While the DNA/gold suspension was being prepared, one 7" length of Tefzel™ (ethylene tetrafluoroethylene) tubing for each sample was pre-dried by insertion into the flexible tubing attached to the manifold drier (as described in U.S. patent application 2017-0130238, published May 11, 2017) and left for at least fifteen minutes with 0.5-0.6 LPM nitrogen flowing through to eliminate environmental humidity accumulation from the inside of the Tefzel™ tubing.

After preparing the DNA/gold suspension and pre-drying the Tefzel™ tubing, the flexible tubing was disconnected from the manifold drier at the Leur lock and attached to a 10 mL syringe. The DNA/gold suspension was mixed well and drawn into the Tefzel™ tubing by application of suction by the syringe. While still connected to the syringe, the Tefzel™ tubing was laid on a flat surface for five minutes while the gold settles out of solution and adheres to the inside of the tubing. After five minutes of settling time, pressure was applied with the syringe to gently push the ethanol out of the tubing. The tubing was immediately turned over to allow the remaining gold slurry to smear to the side of the Tefzel™ tubing opposite where it originally settled. After 2-5 minutes of air drying time, the Tefzel™ tubing was detached from the syringe and moved back onto the manifold drier with 0.5-0.6 LPM nitrogen flowing. When the gold was completely dried as evidenced from a visible color change from dark to light yellow, the Tefzel™ tubing was removed from the flexible tubing and cut into half-inch pieces for use in the Helios® Gene Gun.

To prepare cells for transformation, a 100 mL seed culture inoculated to 0.05 OD730 six days before transformation was used to inoculate a 500 mL culture to 0.2 OD730 one day before transformation. Cultures were grown in commercially available algal growth media in a Conviron™ Incubator at 25 C 1% CO2 shaking at 130 rpm in a 16:8 light:dark cycle.

On the day of transformation, cell cultures were pelleted by centrifugation at 5000×g for twenty minutes. Cells were resuspended in 50 mL osmoticum (250 mM mannitol/250 mM sorbitol 0.1 um filter-sterilized) and incubated for 1-2 hours at room temperature.

After osmotic pre-treatment, cells were concentrated to 20.0 OD730/mL in osmoticum, and 200 uL of cell suspension was painted in each of five 4 cm-diameter circles on a 13 cm-diameter shooting plate containing 2% agar PM147 solid medium. When the cells were completely dried, the Helios® Gene Gun was used to fire two bullets per cell circle at 400 psi from a distance of 3-6 cm from the plate. In total for each sample, 10 replicate bullets were fired at 20.0 OD730 of cells, divided among 5 cell circles. Cells were left on the shooting plates overnight in a dark 30C incubator.

The day after transformation, cells from replicate cell circles were pooled together by washing the shooting plates with liquid standard algal growth media. Recovered cells were plated onto selective media (standard algal growth media containing 425 mg/L blasticidin) at an intended density of 10.0 OD730 per 13 cm-diameter plate.

The *Oocystis* sp. strains having the deletion of the sequence encoding the methyltransferase of SEQ ID NO: 28 were identified as STR28031 and STR29997. Note that these strains differ only in that '031 contains BSD as selectable marker and '997 contains nourseothricin as selectable marker. A substantial decrease in CHG and CHH methylation was noted for the deletion strain, as shown in FIG. 5. The background control strain was STR24194 (except that it had the corresponding selectable marker for comparison of methylation at the transgene).

Figure 10:
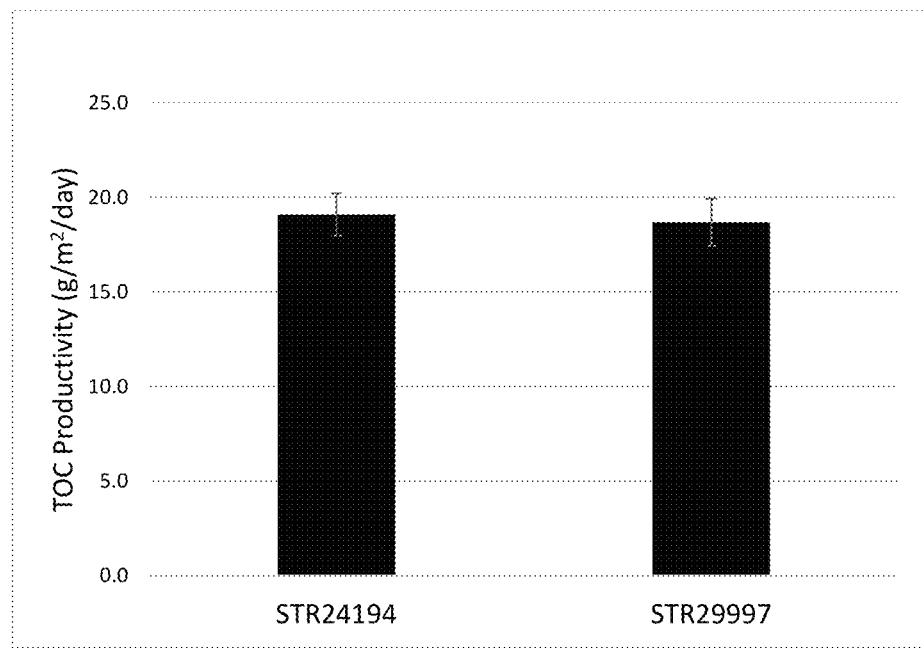
FIG. 10 shows the results of a productivity assay in *Oocystis* sp. (STR29997, having a deletion of the methyltransferase of SEQ ID NO: 29) measured as total organic carbon (TOC) as an indicator of productivity under semi-continuous areal culture. The data show no defects in productivity for the cell compared to background strain (STR24194), which was improved and selected from the wild-type for growth characteristics.

An assay of productivity (FIG. 10) for *Oocystis* sp. (STR29997) and measured as TOC showed no defects in productivity for the cell compared to background strain (STR24194).

Although the invention has been described with reference to the above examples, it will be understood that modifications and variations are encompassed within the spirit and scope of the invention. Accordingly, the invention is limited only by the following claims.

What is claimed is:

1. A mutant photosynthetic organism comprising a mutated or attenuated gene encoding a polypeptide having a CHG DNA methyltransferase activity, wherein the mutation or attenuation is in the gene that encodes the polypeptide comprising an amino acid sequence having at least 80% identity to an amino acid sequence of any of SEQ ID NO: 1, 3, 5, 7 or 28, and wherein the mutant photosynthetic microorganism has reduced CHG DNA methylation as compared to a control photosynthetic organism without a mutated or attenuated gene encoding a polypeptide having a CHG DNA methyltransferase activity.

2. The mutant photosynthetic organism of claim 1, wherein the mutant is a genetically engineered mutant.

3. The mutant photosynthetic organism of claim 2, wherein the mutant has been genetically engineered by insertional mutagenesis, gene replacement, RNAi, antisense RNA, meganuclease genome engineering, one or more ribozymes, and/or a CRISPR/Cas system.

4. The mutant photosynthetic organism of claim 3, wherein the mutant has been genetically engineered by a CRISPR/Cas system.

5. The mutant photosynthetic organism of claim 1, wherein the mutant has been generated by UV irradiation, gamma irradiation, or chemical mutagenesis.

6. The mutant photosynthetic organism of claim 1, wherein the polypeptide having a CHG DNA methyltransferase activity comprises an amino acid sequence having at least 80% identity to an amino acid sequence of SEQ ID NO: 1 or SEQ ID NO: 28.

7. The mutant photosynthetic organism of claim 1, wherein the mutant photosynthetic organism further comprises an exogenous DNA, and wherein the reduced CHG DNA methylation is in the exogenous DNA.

8. The mutant photosynthetic organism of claim 7, wherein the exogenous DNA is integrated into the genome of the photosynthetic organism.

9. The mutant photosynthetic organism of claim 1, wherein the reduced CHG DNA methylation is in a DNA sequence native to the photosynthetic organism.

10. The mutant photosynthetic organism of claim 9, wherein the wherein the reduced CHG DNA methylation is in the centromere or highly repetitive DNA regions of the mutant photosynthetic organism.

11. The mutant photosynthetic organism of claim 7, wherein the expression of the exogenous nucleic acid is greater as compared to a control photosynthetic organism comprising the exogenous nucleic acid but without a mutated or attenuated gene encoding a polypeptide having a CHG DNA methyltransferase activity.

12. The mutant photosynthetic organism according to claim 1, wherein the mutant photosynthetic organism has reduced monomethylation or trimethylation of lysine 9 of histone H3 (H3K9).

13. The mutant photosynthetic organism according to claim 1, wherein the mutant photosynthetic organism has reduced CHH DNA methylation as compared to a control photosynthetic organism without a mutated or attenuated gene encoding a polypeptide having a CHG DNA methyltransferase activity.

14. The mutant photosynthetic organism according to claim 1, wherein the photosynthetic organism is algae.

15. A method of enhancing the expression of an exogenous DNA in a photosynthetic organism, comprising:
   a) introducing an exogenous DNA into the photosynthetic organism;
   b) mutating or attenuating a gene encoding a polypeptide having a CHG DNA methyltransferase activity, wherein the mutation or attenuation is in the gene that encodes the polypeptide comprising an amino acid sequence having at least 80% identity to an amino acid sequence of any of SEQ ID NO: 1, 3, 5, 7 or 28,
   wherein the mutant photosynthetic organism has reduced CHG DNA methylation of the exogenous DNA as compared to a control photosynthetic organism comprising the exogenous DNA but without a mutated or attenuated gene encoding a polypeptide having a CHG DNA methyltransferase activity; and
   wherein the expression of the exogenous DNA is enhanced in the photosynthetic organism as compared to the control photosynthetic organism.

16. The method of claim 15, wherein the mutating or attenuating of the gene encoding a polypeptide having a CHG DNA methyltransferase activity is by genetic engineering.

17. The method of claim 16, wherein the genetically engineering is by insertional mutagenesis, gene replacement, RNAi, antisense RNA, meganuclease genome engineering, one or more ribozymes, and/or a CRISPR/Cas system.

18. The method of claim 17, wherein the genetically engineering is by a CRISPR/Cas system.

19. The method of claim 15, wherein the mutating or attenuating of the gene encoding a polypeptide having a CHG DNA methyltransferase activity is by UV irradiation, gamma irradiation, or chemical mutagenesis.

20. The method of claim 15, wherein the polypeptide having a CHG DNA methyltransferase activity comprises an amino acid sequence having at least 80% identity to an amino acid sequence of SEQ ID NO: 1 or SEQ ID NO: 28.

21. The method of claim 15, wherein the mutant photosynthetic organism has reduced CHH DNA methylation as compared to a control photosynthetic organism without a mutated or attenuated gene encoding a polypeptide having a CHG DNA methyltransferase activity.

22. The method of claim 15, wherein the exogenous DNA is integrated into the genome of the photosynthetic organism.

23. The method of claim 15, wherein the photosynthetic organism is algae.

* * * * *

SEQUENCE LISTING

```
<160> NUMBER OF SEQ ID NOS: 29

<210> SEQ ID NO 1
<211> LENGTH: 1253
<212> TYPE: PRT
<213> ORGANISM: Parachlorella sp.
<220> FEATURE:
<221> NAME/KEY: misc_feature
<223> OTHER INFORMATION: Protein_EMRE3EUKT598198 methyltransferase

<400> SEQUENCE: 1

Met Glu Leu Phe Gly Leu Lys Gly Gln Ala Leu Gln Arg Pro Asp Glu
1               5                   10                  15

Leu Cys Asn Leu Asp Asp Trp Arg Lys Leu Asn Lys Ala Gly Asp Thr
            20                  25                  30

Ser Trp Leu Gly Ser Pro Ile Pro Lys Asp Leu Ala His Thr Leu Tyr
        35                  40                  45

Pro His Arg Lys Tyr Leu Ala Met Glu Ser Leu Ser Asn Arg Lys Gln
    50                  55                  60

Glu Ile Gln Lys Tyr Glu Glu Asp Asn Gly Ser Asp Pro Lys Trp
65                  70                  75                  80

Thr Asp Ala Lys Ala Val Ala His Phe Trp Gly Ala Glu Leu Asp Ser
                85                  90                  95

Leu Phe Asp Asp Thr Gly Asp Leu Ile Pro Gly Phe Lys Leu Tyr
            100                 105                 110

Val Gly Asp Phe Val Arg Leu Asp Leu Gly Glu Gly Arg Lys Gly Val
        115                 120                 125

Cys Gln Val Leu Glu Leu Tyr Gln Asp Pro Leu Gly Ala His Arg Ile
    130                 135                 140

Ser Ile Lys Trp Phe Phe Ser Met Tyr Asp Asp Glu Val Lys Ile Leu
145                 150                 155                 160

Asp Glu Ile Leu Gly Gly Leu Asp Lys Arg Gln Leu Trp Gly Met Leu
                165                 170                 175

Lys Ala Asp Lys Gln Thr Phe Gly Thr Glu Tyr Glu Leu Asn Val Val
            180                 185                 190

Glu Ala Pro Val Lys Val Val Gln Val Leu Pro Gly Glu Thr Pro Pro
        195                 200                 205
```

-continued

Glu Asp Glu Asp Thr Tyr Trp Trp Glu Ser Val His Gly Pro Thr Cys
    210                 215                 220
Tyr Thr Phe Glu Asn Pro Gly Asp Leu Val Pro Thr Ser Arg Thr Arg
225                 230                 235                 240
His Ser Ser Thr Ala Arg Leu Leu Arg Val Met Asp Leu Tyr Ala Gly
            245                 250                 255
Gly Gly Gly Leu Gly Tyr Leu Asp Thr Arg Thr Glu Lys Val Glu Ile
                260                 265                 270
Arg Thr Asp Trp Ala Val Asp Tyr Glu Gln Asp Met Arg Asn Thr Phe
        275                 280                 285
Lys Cys Asn Phe Gln His Ala His Ala Phe Ala Ser Gly Thr Asp Glu
290                 295                 300
Ala Leu Gly Leu Phe Lys Met Val Phe Trp Leu Cys Gln Glu Met Gly
305                 310                 315                 320
Val Gly Lys Glu Ala Val Asp Gly Arg Phe Ser Lys Pro Phe Ala Phe
                325                 330                 335
Asp Lys Leu Glu Arg Cys Asp Asp Gln Met Val Ala Pro Pro Cys
            340                 345                 350
Ser Leu Val Leu Gln Asn Arg Ala Cys Gly Arg Gly Ala Gly Arg
        355                 360                 365
Gln Gln Glu Leu Pro Ala Lys Ala Gln Gly Arg Gly Ala Lys Arg Lys
    370                 375                 380
Arg Val Glu Pro Thr Val Gln Ala Ser Arg Leu His Leu Asp Ser Ser
385                 390                 395                 400
Asp His Glu Ala Cys Ala Glu Ala Glu Val Gly Gly His Ser Gln Gly
                405                 410                 415
Ser Ser Ser Gln Gly Thr Leu Phe His Thr Ala Asp Glu Lys Ser Ser
            420                 425                 430
Arg Gly Glu Gly Glu Glu Gly Ala Asp Ala Ser Arg Val Ala Thr Arg
        435                 440                 445
Asn Gly Arg Thr Cys Ala Ala Thr Gly Gly Gly Gln Thr Gly Gly Lys
    450                 455                 460
Val Gln Ala Lys Ser Leu Arg Ala Ser Lys Ser Lys Pro Gly Ala Lys
465                 470                 475                 480
Asp Gly Val Gly Val Ala Ser Pro Lys Ser Ala Lys Ser Asn Lys Met
                485                 490                 495
Val Ser Arg Ala Glu Ala Glu Ala Lys Asn Thr Ala Trp Pro Ala Ala
            500                 505                 510
Ala Pro Ile Pro Lys Ala Gly Glu Leu Glu Ala Ile Leu Gln Val Arg
        515                 520                 525
Leu Cys Glu Lys Gly Ala Arg Leu Pro Lys Asp Ser Asn Val Gly Ala
530                 535                 540
Ala Gln Leu Ile Arg Glu Ile Arg Pro Glu Glu Met Arg Leu Glu Phe
545                 550                 555                 560
Lys Val Arg Trp Ser Pro Ala Ala Lys Lys Tyr Gly Asp Ser Arg Gly
                565                 570                 575
Glu Ser Trp Leu Pro Arg Ser Ala Leu Gly Ala Tyr Gln Glu Gln Leu
            580                 585                 590
Lys Ser Phe Cys Leu Lys Leu Arg Arg Cys Ser Val Val Pro Phe Pro
        595                 600                 605
Gly Glu Val Asn Leu Ile Cys Gly Gly Pro Pro Cys Gln Gly Val Ser
    610                 615                 620

```
Gly Asn Asn Arg His Ala Lys Met Arg Asp Ile Leu Gln Asp Val Arg
625                 630                 635                 640

Asn Arg Gln Leu Leu Val Phe Leu Asp Phe Val Lys Trp Phe Lys Pro
            645                 650                 655

Asn Phe Val Leu Met Glu Asn Val Gln Asp Ile Met Lys Lys Glu Glu
            660                 665                 670

Gly Lys Tyr Val Lys Tyr Ala Met Gly His Thr Leu Gln Met Gly Tyr
            675                 680                 685

Gln Ile Arg Leu Gly Leu Leu Ala Ala Gly Asp Phe Gly Val Ser Gln
690                 695                 700

Gly Arg Trp Arg Cys Phe Met Trp Gly Ala Leu Lys Asn Glu Glu Gln
705                 710                 715                 720

Leu Pro Ala Phe Pro Glu Ala Thr His Asn Cys Arg Asn Phe Lys Thr
            725                 730                 735

Gly Val Cys Thr Leu Gly Lys Asp Cys Gln Gly Gly Phe Leu Ser Asp
            740                 745                 750

Glu Asn Ser Leu Glu Ala His Pro Pro Val Leu Gly Asp Val Met
            755                 760                 765

Ala Asp Leu Pro Glu Val Thr Asn Gly Glu Leu Arg Glu Arg Leu Ser
770                 775                 780

Tyr Pro Cys Asp Pro Lys Tyr Val Gln Gln Met Trp Tyr Arg Arg Leu
785                 790                 795                 800

Pro Gln Pro Trp Gln Thr Ser Ile Glu Glu Arg Ile Ala Phe Arg Ser
            805                 810                 815

Glu Val Leu Glu Lys Gln Gln Leu Lys Phe Asn Arg Glu Leu Leu Glu
            820                 825                 830

Ser Val Lys Thr Asp Glu Asp Val Thr Gln Leu Gly Leu Arg Ser Leu
            835                 840                 845

Asn Thr Lys Asn Pro Leu Lys Gly Ala Glu Gln Asn Asn Lys Pro Lys
850                 855                 860

Leu Arg Gln Asp Gly Thr Gln Ala Gly Asn His Pro Phe Glu Thr Ile
865                 870                 875                 880

Thr Ala Ala Leu Arg Met Leu Ser Asn Pro Arg Glu Ala Glu Ile Leu
            885                 890                 895

Lys Leu Glu Met Glu Ala Gly Arg Leu Cys Phe Ala His Glu Arg Gly
            900                 905                 910

Met Gln Ile Tyr Lys Glu Leu Gln Glu Tyr Leu Lys Glu Ser Glu Arg
            915                 920                 925

Gly Leu Gly Ser Gly Gln Val Leu Cys Asp His Arg Pro Leu Ile Leu
930                 935                 940

Asn Asp Asp Asp Tyr Leu Arg Ile Thr Val Val Pro Lys Arg Thr Arg
945                 950                 955                 960

Tyr Glu Glu Glu Glu Asp Arg Leu Cys Asn Phe Arg Ala Leu Glu Gly
            965                 970                 975

Val Val Asn Asn Ala Asp Gly Thr Cys Cys Tyr Gly Ser Gln His Ala
            980                 985                 990

Glu Arg Arg Lys Asp Gly Thr Ser  Gly Cys Lys Gly Gly  Gly Thr Tyr
            995                 1000                 1005

Thr Ile  Asp Lys Arg Ser Asn  Ala His Val Thr Arg  Ile Asp Gln
            1010                1015                 1020

Glu Asp  Lys Asn Gly Trp Arg  Gly Val Ala Leu Gln  Gly Cys Gln
            1025                1030                 1035

Ala Tyr  Val Lys His Leu Pro  Thr Met Glu Pro Glu  Leu Pro Arg
```

```
                    1040                1045                1050
Trp Cys Val Thr Phe Lys Arg Gly Lys Ser Asp Gly Arg His Gly
        1055                1060                1065
Gly Phe Gly Arg Val His Phe Ser Gln Ile Ile Thr Thr Val Ile
    1070                1075                1080
Gly Arg Ala Glu Pro His Asn Leu Lys Leu Ala His Pro Thr Gln
    1085                1090                1095
Asp Arg Val Met Thr Ile Arg Glu Asn Ala Arg Cys Gln Gly Phe
    1100                1105                1110
Pro Asp Tyr His Val Phe Cys Ala Asp Leu Ser Arg Gly Gly Arg
    1115                1120                1125
Asn Arg Trp Val Arg Asn Ser Thr Leu Thr Gln Arg Tyr Gln Met
    1130                1135                1140
Ile Gly Asn Ala Val Cys Pro Glu Val Ala Ser Ala Leu Gly Arg
    1145                1150                1155
Cys Leu Ala Leu Ala Ala Thr Gly Glu Ser Pro Gly Glu Cys
    1160                1165                1170
Tyr Ile Gln Val Pro Asn Pro Ala Tyr Leu Gln Val Val Lys Ala
    1175                1180                1185
Ala Arg Glu Lys Gly Leu Glu Tyr Phe Phe Glu Glu Tyr Val Arg
    1190                1195                1200
Glu His Pro Arg Gly Tyr His Ser Ile Ser Leu Glu Ala Arg Leu
    1205                1210                1215
Cys Ala Ala Ala Glu Gly Tyr Ile Pro Gln Gly Gly Ser Ser Gly
    1220                1225                1230
Thr Gly Ala Val Asp Asp Glu Asp Glu Val Asp Asp Asp Ser Gln
    1235                1240                1245
Gly Glu Glu Gly Asp
    1250

<210> SEQ ID NO 2
<211> LENGTH: 3761
<212> TYPE: DNA
<213> ORGANISM: Parachlorella sp.
<220> FEATURE:
<221> NAME/KEY: misc_feature
<223> OTHER INFORMATION: EMRE3EUKC598198, cDNA for methyltranferase of
      SEQ ID 1

<400> SEQUENCE: 2
atggaattat tcggccttaa aggtcaagcc ttacagcgtc cagatgagct ttgtaacctg        60
gatgattgga gaaagctgaa taaagcaggc gacacgtcat ggcttggctc acctatcccc       120
aaggaccttg ctcacacctt gtatccacac cgcaagtacc tggccatgga aagcttgagc       180
aatcgcaagc aagaaatata gaaatacgag gaagaagata atggcagcga tccgaaatgg       240
acagatgcaa aagcagtggc tcacttctgg ggcgcggagc tggatagcct gtttgatgat       300
gacaccgggg acctcatccc aggtttcaag ctgtatgttg cgactttgt caggcttgat       360 cttggggaag gacgaaaagg cgtctgccag gttctcgagc tctaccagga tcccttgggg       420
gcacatcgca tcagcatcaa gtggtttttc agcatgtacg acgatgaggt gaagattcta       480
gatgagattc tgggggggct ggacaagagg cagttgtggg gcatgcttaa ggcagacaaa       540
cagacgtttg gacggaata cgagctcaat gttgtggagg cacctgttaa agttgttcag       600
gtgcttccgg gagagacccc cccagaggat gaagatacgt actggtggga atcagttcat       660
ggtcccacct gctacacctt tgagaatccc ggggaccttg tccccaccag caggaccaga       720
```

| | |
|---|---|
| cactccagca ctgcgaggct gctgcgagtg atggacctgt atgccggagg cggtggcctt | 780 |
| ggatacctgg acacgcgcac tgagaaagtg gagatcagga ccgattgggc tgtggactac | 840 |
| gagcaagaca tgaggaacac gttcaaatgc aacttccagc atgcccacgc ctttgctagc | 900 |
| ggcactgacg aagcactggg gctcttcaaa atggtattct ggctgtgcca agaaatgggt | 960 |
| gtgggcaaag aagctgtgga tgggagattc tcaaagccgt ttgcgtttga caagcagagc | 1020 |
| gatgcgacga tgaccagatg gtggcccctc cctgctcctt ggttctccag aacagggcgt | 1080 |
| gcggcagagg gagggcagga aggcagcagg agctgcctgc aaaggcacaa ggcagggggg | 1140 |
| cgaaacgaaa gcgagtggag ccaactgtgc aagcaagcag gctgcacctg gactcctccg | 1200 |
| atcatgaggc ctgtgccgag gcagaggtgg gaggtcacag ccaggggagc agctcccagg | 1260 |
| ggactttgtt ccacacagct gatgagaaga gcagccgagg cgaaggtgaa gaaggcgccg | 1320 |
| atgcgtccag ggtggccaca aggaatggac gcacatgtgc agccacaggt ggaggccaaa | 1380 |
| caggggggaa ggtgcaggcc aagagtttaa gagcaagcaa gagcaaacct ggcgcgaaag | 1440 |
| atggagttgg tgttgcgtcc cctaaatctg caaagagcaa taagatggtg agcagagctg | 1500 |
| aggccgaggc caagaacacg gcatggccag ctgcggcacc catcccgaaa gctggggagt | 1560 |
| tggaagcaat cttgcaagtc aggctgtgcg agaagggcgc ccggctacct aaggactcca | 1620 |
| acgtgggggc tgcacagctc attagagaga tacggccgga agaaatgcgc ctggaattca | 1680 |
| aggtgaggtg gtcgccagct gcgaagaagt atggggacag caggggggaa agctggctac | 1740 |
| ctcgcagtgc gcttggcgcc taccaagaac agctcaagag cttctgcctc aagctccgaa | 1800 |
| ggtgctccgt ggtgcctttc ccgggggagg tcaacctcat ctgcggaggg ccccctgcc | 1860 |
| agggagttag tgggaacaac cggcatgcca agatgcggga catcctgcaa gacgtcagga | 1920 |
| atcgccagct gctggtgttt ctggactttg tgaagtggtt caaaccgaac tttgtcctca | 1980 |
| tggagaatgt gcaggacatc atgaagaagg aggagggcaa gtatgtcaag tatgctatgg | 2040 |
| ggcacacact gcagatgggg taccagatcc gtctggggct gctggctgcg ggcgactttg | 2100 |
| gcgtgtccca gggcaggtgg aggtgcttca tgtgggggc tctgaagaat gaggagcagc | 2160 |
| tgccggcatt ccccgaggca acgcacaact gccgaaactt caagaccggc gtgtgcacgc | 2220 |
| tgggcaagga ctgccaggga ggcttcctgt ctgacgagaa cagcctcgag gcccacccc | 2280 |
| cggttctgtt gggggacgtg atggccgacc tcccagaggt gacaaacggc gagctgcggg | 2340 |
| agaggctgag ctaccctgc gaccccaaat atgtgcagca gatgtggtac aggcgtctgc | 2400 |
| ctcagccttg gcagacttcc atagaggagc gtattgcctt cagatcggag gttctggaga | 2460 |
| agcagcagct gaaattcaac agggaactgc tggaaagtgt gaaaacagac gaagatgtca | 2520 |
| cacagctggg cctgcgctcc ctgaacacca agaaccccct aaaaggggcg gagcagaaca | 2580 |
| acaagccaaa gctgcggcaa gacggcaccc aagcaggtaa tcacccctt gagacgatca | 2640 |
| ccgctgcgct gcgcatgctg agcaaccccca gggaggccga gatcctgaag ctggagatgg | 2700 |
| aggctggcag gctgtgcttt gcacacgagc ggggatgca gatctacaag gagttacagg | 2760 |
| agtacctgaa ggagtctgag cgtggcctgg ggtctggcca ggttctgtgt gaccaccgac | 2820 |
| cactcattct caatgatgac gactacctcc gcatcacggt ggtgcctaaa cggaccaggt | 2880 |
| atgaggagga ggaggaccgg ctgtgcaact tcagagcgct cgagggagtc gtgaacaacg | 2940 |
| cagatggcac gtgctgctat gggagtcagc atgcggagag gaggaaagac ggcacatctg | 3000 |
| ggtgcaaggg aggggcacg tataccattg acaagcggag caatgcccac gtcacccgca | 3060 |

```
tcgaccagga ggacaagaat gggtggaggg gtgtggcgct acaagggtgc caggcgtacg    3120
tgaagcactt gcccacgatg gagccggagc tgcctcggtg gtgcgtcacc ttcaagcgcg    3180
gcaagtcaga cgggcggcat ggcggctttg ccgtgtgca cttctcgcag atcatcacca     3240
cggtgatagg acgggcagag ccgcacaact tgaagctggc ccaccccacg caagacaggg    3300
tgatgaccat cagggagaac gcacgttgcc agggcttccc tgattaccac gtattctgtg   3360
cggacctctc ccgtggcggc cgcaatcgct gggtccgcaa ctccaccctc acacagcgct   3420
atcagatgat cgggaacgcg gtttgcccgg aggtggcatc tgcacttggc cgctgcctgg   3480
ctcttgctgc cactggggag agccccccg gggaatgcta catccaggtc cccaaccctg    3540
cgtacctcca ggttgtgaag gcggccaggg agaagggct ggagtacttc tttgaggagt    3600
atgtgaggga gcacccaagg ggatatcaca gtatttcgct ggaggcaagg ctgtgcgcgg   3660
cggctgaggg gtatattccg cagggaggga gtagtggaac gggtgctgtc gatgatgaag   3720
atgaggtaga cgatgacagt cagggagaag agggtgattg a                        3761
```

<210> SEQ ID NO 3
<211> LENGTH: 1717
<212> TYPE: PRT
<213> ORGANISM: Parachlorella sp.
<220> FEATURE:
<221> NAME/KEY: misc_feature
<223> OTHER INFORMATION: methyltransferase, Protein_EMRE3EUKT590754 methyltransferase

<400> SEQUENCE: 3

```
Met Pro Ala Asn Lys Gly Lys Ala Tyr Val Glu Val Gly Lys Asp Gly
1               5                   10                  15

Thr Leu Pro Ala Leu Met Ala Gly Lys Gln Gly Lys Arg Glu Ala Ser
            20                  25                  30

Glu Lys Leu Pro Ala Lys Glu Pro Ala Lys Ala Lys Lys Glu Gln
        35                  40                  45

Pro Ala Lys Glu Ala Asp Gly Glu Val Lys Val Ala Lys Asp Thr Ala
    50                  55                  60

Val Lys Glu Glu Ala Thr Val Val Gly Ser Gly Arg Val Ala Ala Gln
65                  70                  75                  80

Lys Leu Ser Leu Lys Glu Ala Ala Val Lys Val Ser Asn Lys Ala Asp
                85                  90                  95

Lys Ile Ile Ile Lys Glu Glu Val Lys Cys Gly Gly Glu Arg Glu Ala
            100                 105                 110

Leu Glu Ala Thr Ala Gly Thr Thr Pro Ala Asp Tyr Gln Arg Arg Leu
        115                 120                 125

Gly Asp Phe Ser Val Val Asp Asn Glu Gly Lys Ala Glu Pro Ile Asp
    130                 135                 140

Ser Val Gly Leu Gly Ser Lys Asp Leu Phe Ile Ser Gly Val Val Tyr
145                 150                 155                 160

Pro Arg Glu Gly Glu Ala Asn Lys Gln Ser Gly Arg Arg Val Glu Arg
                165                 170                 175

Val Gly Pro Leu Arg Gly Phe Phe Leu Asp Leu Ala Gly Lys Thr Ala
            180                 185                 190

Gln Leu Ile Leu Glu Thr Gln Leu Ala Lys Tyr Val Cys Leu Arg Pro
        195                 200                 205

Ala Pro Thr Tyr Lys Lys Leu His Ala His Leu Ala Glu Gln Ala Asp
    210                 215                 220

Ile Cys Cys Glu Val Phe His Ala Leu Ser Val Gln Asn Gly Gly Ser
```

```
                225                 230                 235                 240
        Pro Gln Thr Ser Leu Glu Glu Val Val Ala Arg Leu Ala Arg Thr Lys
                        245                 250                 255
        Leu Ser Arg Gly Tyr Pro Ser Ala Arg Glu Ala Val Leu Leu Asn Gly
                        260                 265                 270
        Lys Phe Leu Ile Ala Gln Leu Gly Lys Gln Met Gly His Lys Gly Phe
                        275                 280                 285
        Cys Tyr Ala Asp Thr Glu Phe Cys Lys Thr Leu Ala Glu Glu Met Lys
                        290                 295                 300
        Ser Phe Lys Tyr Val Gly Ser Gln Lys Gln Asn Thr Gly Ile Val Ile
        305                 310                 315                 320
        Arg Asp Ala Gln Pro Ala Lys Thr Ala Val Ala Ser Glu Ala Asp Ala
                        325                 330                 335
        Gln Leu Ala Ala Asp Glu Glu Phe Ala Arg Gln Met Gln Ala Lys Glu
                        340                 345                 350
        Asp Ala Arg Ala Arg Gly Pro Arg Leu Ala Ala Val Pro Lys Gly Ala
                        355                 360                 365
        Lys Gly Ala Gln Ala Tyr Ile Lys Val Ser Glu Ala Glu Ile Ala Asp
                        370                 375                 380
        Asp Tyr Pro Ala Pro Thr Pro Tyr Thr Lys Glu Glu Glu Met Asp
        385                 390                 395                 400
        Glu Leu Leu Leu Phe Asp Glu Glu Leu Met Asp Val Asp Pro Glu Phe
                        405                 410                 415
        Leu Pro Arg Arg Leu Leu Thr Asp Phe Thr Ile Tyr Asn Ala Glu Gly
                        420                 425                 430
        Phe Asn Ala Ser Leu Glu Leu Leu Pro Met Trp Ala Gly Leu Asp Ser
                        435                 440                 445
        Asp Val Glu Leu Tyr Ala Ser Gly Val Val Asp Asp Gly Glu
                        450                 455                 460
        Trp Ala Gly Gly Gln Ala Leu Glu Glu Ala Pro Ala Pro Pro Gly
        465                 470                 475                 480
        Ala Gly Gly Ser Gly Ser Ser Gly Ala Gly Ser Gly Ala Gly Ser
                        485                 490                 495
        Ser Ser Ala Thr Ala Gly Gly Ser Ser Ala Glu Ala Ala Pro Glu Gln
                        500                 505                 510
        Gly Gly Met Arg Met Tyr Leu Ser Gln Ile Arg Glu Trp Ile Val Glu
                        515                 520                 525
        Cys Ser Cys Asp Gln Leu Phe Ile Ser Ile Arg Thr Asp Val Ala Trp
                        530                 535                 540
        Tyr Arg Leu Ser Thr Pro Ala Glu Lys Tyr Lys Pro Trp Phe Gly Thr
        545                 550                 555                 560
        Val Leu Lys Cys Ala Arg Val Ala Val Lys Val Leu Gly Met Leu Ser
                        565                 570                 575
        Ala Glu Ala Arg Ala Ser Arg Leu Ser Phe Asn Asp Val Ile Lys Arg
                        580                 585                 590
        Leu Ala Glu Leu Glu Glu Gly Thr Pro Thr Phe Ile Ser Ala Lys Leu
                        595                 600                 605
        Pro Ala Val Gln Arg Phe Val Val His Gly Gln Ile Ile Leu Asn
                        610                 615                 620
        Gln Phe Gln Asn Tyr Pro Ser Asp Ala Val Arg Arg Ser Ala Phe Val
        625                 630                 635                 640
        Ser Gly Leu Lys Glu His Met Gln Met Val Arg His Ser Lys Leu Tyr
                        645                 650                 655
```

```
Lys Ser Ser Ala Lys Val Val Arg Arg Ala Val Asn Arg Asn Pro
            660             665             670

Met Lys Asp Arg Ala Ala Gly Arg Lys Ser Lys Pro Met Thr Ala Thr
    675             680             685

Ala Thr Ser Met Val Lys Ser Ile Trp Gln Ser Tyr Phe Asn Val Gly
690             695             700

Glu Ala Gln Ala Ala Ala Glu Asp Ala Pro Ala Ala Lys Glu Val
705             710             715             720

Glu Glu Asp Glu Asn Glu Glu Asn Glu Glu Val Gln Glu Asp
            725             730             735

Ala Leu Ala His Ala Ala Ser Pro Ala Pro Ala Lys Lys Ala Val Gly
            740             745             750

Lys Lys Gly Ala Ala Lys Lys Glu Gly Gly Ser Ala Lys Val Ala Trp
            755             760             765

Val Gly Gly Val Glu Lys Thr Val Glu Gly Asp Lys Phe Tyr Ala Lys
            770             775             780

Ala Lys Val Gly Asp Leu Gln Val Ser Leu Gly Ala Val Val Ala Met
785             790             795             800

Gln Pro Glu Gly Asp Glu Glu Gly Glu Gly Glu Glu Gly Gly Gln
            805             810             815

Glu Ala Pro Leu Gly Leu Val Gln Ala Met Trp Gln Ser Lys Lys Gly
            820             825             830

Glu Lys Gln Val Gln Val Arg Val Met Val Arg Gly Cys Glu Thr Val
            835             840             845

Leu Gly Asp Ala Ala Ser Gly Glu Leu Phe Leu Thr Thr Arg Leu
            850             855             860

Glu Thr Arg Ala Leu Gly Gly Val Met Gly Val Ile Asn Ala Arg Gln
865             870             875             880

Leu Thr Arg Gly Thr Glu Ala Thr Met Arg Leu His Tyr Ala Lys Glu
            885             890             895

Asp Ala Glu Leu Arg Gln Arg Asn Gln Glu Ala Ala Met Glu Gly Gln
            900             905             910

Pro Leu Glu Phe Ile Trp Arg Arg Gln Tyr Val Pro Glu Gln Gly Met
            915             920             925

Phe Arg Asp Pro Gln Arg Asp Leu Gln Leu Gly Thr Arg Leu Gln Glu
            930             935             940

Glu Ala Gly Ala Gln Lys Gly Val Gln Ala Leu Glu Gly Gly Lys Gly
945             950             955             960

Phe Thr Lys Asp Gly Val Glu Tyr Arg Glu Gly Asp Phe Leu Tyr Val
            965             970             975

Ser Pro Gly Val Phe Asp Arg Val Glu Ala Asp Glu Glu Arg Glu Leu
            980             985             990

Pro Glu Tyr Leu Ala Asn Ser Arg Phe His Lys Gly Ser His Asp Gly
            995             1000            1005

Leu Arg Ala Trp Gly Ile Gly Gln Leu Val Arg Leu Gly Ala Ala
            1010            1015            1020

Gly Lys Lys Gly Gly Asp Lys Val Ser Asn Leu Thr Leu Arg Arg
            1025            1030            1035

Phe Tyr Arg Pro Glu Asp Val Ser Arg Asp Gln Ala Tyr Arg Ala
            1040            1045            1050

Ala Ser Phe His Glu Val Tyr Ala Ser Glu Glu Gln Val Thr Val
            1055            1060            1065
```

```
Gly Val Glu Asp Val Val Gly Arg Cys Thr Val Pro Glu Gly
    1070                1075            1080

Arg Pro Ala Gly Gly Asn Thr Phe Val Cys Thr Ala Ser Phe Ser
    1085                1090            1095

Arg Lys Gly Lys Lys Phe Gly Pro Ala Pro Lys Ile Glu Ala Pro
    1100                1105            1110

Ala Glu Ala Ser Leu Leu Ala Pro Ala Thr Ala Pro Ala Gly Asp
    1115                1120            1125

Lys Gly Lys Gly Lys Gly Lys Ala Val Met Ala Val Asp Ser Gly
    1130                1135            1140

Lys Ala Ala Pro Ala Leu Lys Lys Phe Ala Gly Asp Asp Gly Ile
    1145                1150            1155

Ala Leu Ala Thr Met Asp Ile Phe Ala Gly Cys Gly Gly Leu Ser
    1160                1165            1170

Glu Gly Met His Gln Ala Gly Ala Ala Phe Thr Lys Trp Ala Ile
    1175                1180            1185

Glu Tyr Glu His Pro Ala Ala Glu Ala Phe Lys Leu Asn Asn Pro
    1190                1195            1200

Asp Ala Ala Val Phe Cys Asn Asn Cys Asn Val Leu Leu His Ala
    1205                1210            1215

Ala Met Thr Lys Ala Gly Leu Gly Asn Asp Cys Met Ala Ser Pro
    1220                1225            1230

Glu Ala Glu Glu Glu Ser Arg Gln Leu Pro Ala Glu Gln Tyr Gly
    1235                1240            1245

Asn Leu Pro Ala Pro Gly Glu Val Asp Phe Ile Cys Gly Gly Pro
    1250                1255            1260

Pro Cys Gln Gly Tyr Ser Gly Met Asn Arg Phe Asn Lys Gly Asn
    1265                1270            1275

Trp Ser Met Val Gln His Gly Arg Ala Ala Gln Cys Ala Ala Val
    1280                1285            1290

Leu Gln Cys Ile Leu Lys Ser Gly Thr Val Val Arg Gly Gly Asp
    1295                1300            1305

Trp Val Pro Ala Pro Ala Cys Phe Ser Ile Leu Thr Pro Phe Val
    1310                1315            1320

Ser Pro Ser Thr Leu Ser Cys Ser Arg Phe Ile Cys Arg Pro Pro
    1325                1330            1335

Pro Cys His Val Gln Asn Ser Met Val Met Ala Phe Leu Ser Tyr
    1340                1345            1350

Cys Asp Phe Tyr Arg Pro Arg Tyr Phe Leu Leu Glu Asn Val Arg
    1355                1360            1365

Asn Phe Val Ser His Asn Lys Ser Phe Thr Phe Arg Leu Thr Leu
    1370                1375            1380

Arg Ser Leu Leu Asp Met Gly Tyr Gln Val Arg Phe Gly Val Leu
    1385                1390            1395

Asn Ala Gly Asn Phe Gly Val Ala Gln Ser Arg Lys Arg Thr Phe
    1400                1405            1410

Ile Trp Ala Ala Ala Pro Gly Glu Leu Leu Pro Asp Trp Pro Gln
    1415                1420            1425

Leu Met His Cys Phe Arg Thr Pro Gln Leu Thr Ile Asn Leu Pro
    1430                1435            1440

Gly Gly Val Gln Tyr Thr Ala Val Pro Gln Thr Val Gly Ala Pro
    1445                1450            1455

Leu Arg Pro Val Thr Val Arg Asp Thr Ile Gly Asp Leu Pro Pro
```

-continued

```
            1460                1465                1470
Ile Gln Asn Gly His Asp Gln Glu Glu Met Asp Tyr Pro Ser Ala
    1475                1480                1485

Pro Val Ser Ala Phe Gln Arg Phe Ile Arg Gly Asp Cys Gln Lys
    1490                1495                1500

Leu Thr Glu His Ile Cys Lys Thr Met Asn Asp Leu Asn Leu Glu
    1505                1510                1515

Arg Cys Arg Cys Ile Pro Lys Asn Val Pro Gly Ala Asp Trp Arg
    1520                1525                1530

Val Leu Glu Glu Ile Val Arg Lys Asp Pro Thr Arg Glu Lys Phe
    1535                1540                1545

Asn Val Ser Pro Pro Ala Val Pro Val Leu Cys Met Leu Gly Gly
    1550                1555                1560

Leu Asp Pro Ala His Gly Gly Gln Gly Cys Thr Cys Val Gly Leu
    1565                1570                1575

His Pro Pro Gln Arg Gly Pro Pro Phe Met Cys Arg Ser Leu Gln
    1580                1585                1590

Gly Gln Pro Leu Val Pro Trp Cys Leu Pro Asn Thr Ala Asp Arg
    1595                1600                1605

His Asn Gly Trp Arg Gly Leu Phe Gly Arg Leu Asp Leu Asn Gly
    1610                1615                1620

His Phe Pro Thr Ser Thr Thr Asp Pro Gln Pro Met Gly Lys Val
    1625                1630                1635

Gly Gln Val Phe His Pro Glu Gln Asp Arg Ile Val Ser Val Arg
    1640                1645                1650

Glu Cys Ala Arg Ala Gln Gly Phe Pro Asp Arg Phe Arg Phe Tyr
    1655                1660                1665

Gly Asn Val His Ser Lys His Arg Gln Val Gly Asn Ala Val Pro
    1670                1675                1680

Pro Pro Leu Ala Ala Ala Leu Gly Arg Gln Leu Arg Lys Ala Leu
    1685                1690                1695

Glu Leu Lys Ala Ser Glu Glu Ala Lys Glu Arg Ile Gln Ala His
    1700                1705                1710

Leu Lys Gly Leu
    1715

<210> SEQ ID NO 4
<211> LENGTH: 5839
<212> TYPE: DNA
<213> ORGANISM: Parachlorella sp.
<220> FEATURE:
<221> NAME/KEY: misc_feature
<223> OTHER INFORMATION: Protein_EMRE3EUKT590754, cDNA for
      methyltransferase of SEQ ID 3

<400> SEQUENCE: 4
ggggtggagg acgtggtggg caggtgcacg gtggtgccgg agggacgccc cgcaggtgag      60 ggggggggcaa atgggggggc ggcagaggcc tgctgcataa tagggacggg gggagaaggg     120
gtgagtagga ggagggccgg atgcctgtgg tacgcatgtg atgctggggg cctggcaggt     180
tggggtcaac tgtggtggat cgcctgcgca atggggttgc tacaccacat caggagcacg     240
tgtcaggggg gtgcggtcag aggctagcgc cggcaaatgc tccccccttt ggcctgtctg     300
ttgagtgcgc agggggcaac acgtttgtgt gcaccgccag cttcagccgc aagggcaaga     360
agtttgggcc cgcacccaag atcgaggcac cggcagaggc gtccctcctc gccccggcta     420
```

-continued

```
ctgctcccgc tggcgacaag ggtgcgctgc catcacgagg accgctttga gagggttgat       480
gtggggcaga aacggggag tttgaggggc acatggggcg cagctgagtg gacgttggat        540
tgatggggtg atggatgggt tgtgagccgt cgccagacga gctgcagctc acggaaaggt       600
gtttagagct tgcggggtgc agggcgcctg ctgggaaaag aggggggggt ccacccctgg       660
ccagccttac acagccctca cctcgacctc ccctccctg gtcacgcatg cgcaggcaag        720
ggcaagggca aggcagtcat ggcggtggac agcggcaagg ctgcccctgc actcaagaag       780
tgagccggca tcattctccc tccccctcc ctctcttccc ctcccctct ccatcctgct         840 gctgccctct ccgcctgccc ggttgatttc cgttccgcgc gcagcgtgcg cccagtgctg       900
ctccctgttt acagccacct ctgcacgcct cttctgtagt cacactcaca tgtggctgtg       960
gtggggagcg cagtcctcca cctctccttc ctttctgcaa aatctctttt ttgacccatc      1020
tgttgcccac tagttgcata cctccctggc agagtcgtgc tcgatcactc ccgggtgcat     1080
ctgctgaaat tgcatgctga ccaagcccaa acgccggtgg tgcaggtttg ctggcgatga     1140
tggcatcgcc ctggccacca tggacatctt tgccgggtgc ggggggctgt cggagggcat    1200
gcaccaggct ggtgagtcac cctccaccc gtgccggccc cccgccccc cctctacac      1260 cctgtctatc tgtactcatt gctgtgcccc atagcaattg ctgtttcgat actgccaaaa     1320
cccaaattcg taaatttgct gccgaccgtg gctctgccgt gccgatcccg gttgctgtgc    1380
ccgtcacgct gtgctctgct gcactgcgct ccaggtgccg ccttcaccaa gtgggccatc    1440
gagtacgagc accccgcggc agaggcgttc aagctcaaca acccggacgc cgctgtgttc   1500
tgcaacaact gcaacgtgct gctgcacgcc gccatgacca aggcggggct gggcaacgac   1560
tgcatggcgt caccagaggt gagctgccga gtggggaggg aagggatgag aatccaggat   1620
tcaacccctg tggggagcag aggggggagg aggctaggtg atgttgtggc agacgcgcta    1680
cagagtagct ggggggaggg ggcttgtgga tggcacggca gtacacggcg gagggtggcg   1740
gggcagtggc cccatgggtt gctggctgcg tctgcaggga gggctgggac catggggggg   1800
tgtctttgac tatccaccac gtggcagcag gcttcatgat gggctgctgg tggtgccccc   1860
acctacagtg agccctggag gtgcgtggct ctctcaggcc gcgggcacgc acacacacgc    1920
acgcacacac ttgtgcttcc ggtttcaggc ggaggaggag agcaggcagc tgccagccga   1980
gcagtacggc aacctgccgg ccccggaga ggtggacttc atctgcggcg ccccccctg     2040 ccagggctac tcggggatga accgattcaa caagggcaac tggtcaatgg tgcaggtaag    2100
ggcggggggg ggatggagag gtggtggggc gcagctcttg gcgcaggggc ttctgctcct   2160
gcagcatggc agggcggcgc agtgtgcagc agtgctccag tgtattttga aaagtggcac    2220
agtggtcagg ggagggggact gggtccctgc accagcttgc ttttccatac tgacacccctt  2280 tgtgtcccca tccacgctct cctgctcacg ttttatttgt cggcctcccc cctgtcatgt    2340
gcagaactcc atggtgatgg ccttcctgtc ctactgcgac ttctaccgcc ccgctacttt    2400
tctgctggag aacgtgcgca actttgtgtc gcacaacaag tcgttcacct tccgcctcac    2460
gctgcgctcg ctgctggaca tggggtacca ggtgtgtgtg tggtgtcagt gggaagattg    2520
caggggttgg aggggcgggg ggcgaccaga cgcgcttgga gccgtgcaag agcgtggcaa    2580
tgtgcgctgt cccccctgt gggaggggct gcctgctgt gcttcgtgtg agcaccccct      2640
ggtgcgcttc atcgaaagat gggagtgtgt gaggaagggg tgtgtgtaaa tgctggtgtg    2700
gagaaggagg ggtgcggtga gggcgtggcc ctgcatgtct cttactcct atggtgcacc    2760 ctttcttcct ccccggccta cgcatgtcct accaccccct gcacccgccc gcccttcgtt   2820
```

```
tcttgtgtac ccatccatgg aggcccagca cacgcctcgc acactcccct aggtgacctt    2880
gttacaacct cctcccctcc ccactccgcc cccaggtggt ttttttttt gcaagatatt     2940 ttcatttatt tatttattta ccctaaacaa ccctcgcaca gcatgcgtgg ctcaattccc    3000
tccccctccc cttgcaggtc cgctttggtg tactgaacgc cggcaacttt ggcgtggccc    3060
agtcccgcaa gcgtaccttc atctgggccg cagcccccgg ggagctgctg ccggactggc    3120
cccagctgat gcactgcttc cgcaccccc agctcaccat caacctgcct ggaggtgggt     3180
gggtgggtgg gtgggtgggc ccgggtgtgt gtgccaaccc gtgtgttgag gagggagggg    3240 gggggggggtc atgtggcttt ggagagatgg gtggagatg cagacgtggg ggggggggg     3300 ggggggatcca atcccctctc ccctccccc tttccccccc cgctgatatg cctgacagca    3360
agggagtttg aggggtgggc gcatgtccat ggcgccgatg ctggagtacc cgatgctatt    3420
tggccccagg aggcaagtgg cagctgccgg agctgttgca gcgagtgctg agcatgccgc    3480
ctcctgctcg gtatagtgtg tgcggcatga cagaggggtc caggaggtgg gaggcaatcg    3540 agtgcccct gtgcgttgct gcctgcaggc gtgcagtaca ccgccgtacc gcagacggtg     3600
ggtgcaccgc tgcgccccgt caccgtgcgc gacaccattg cgacctgcc ccccatccag     3660 aacgggcacg accaggagga aatggactat cccagcgcgc cggtgggtca gcccacacct    3720
gtacctgcac ctctgcctgc acagtgccct ctttgcatcc atcatgagcc ggtgcctatc    3780
cagctcaggc tgccaaaccc agcgtggctc ccctagtctg tagcctcctg gtcttgcctc    3840
gaaaccatcg gcacagccac catcaatgtc tgccttctcc ccccccctc accctccaa     3900 cccccccctt gctggctgct gcaggtgtcg gccttccagc ggttcatccg tggcgactgc    3960
cagaagctga cggagcacat ctgcaagacc atgaacgacc tcaacctgga gaggtgcagg    4020
tgagcggggc ggggtgggag tggggggag aggagggagg gtccgggggg tgggcagagg     4080
ttggaacact caaggttggc atggtggcag ttgccatgtg gcaggtgcaa gccgacgcag    4140
tgcatgtcca ggagtatgtc agtgggtgtc ttcttggccg tgcaaatatt attcagtgtt    4200
gtaggtgcag ttgccagtgc agctgcatca ggcagcagcc atagtggggg aacggtgcag    4260
gggccagcag tggtccaaga gctgggtgtg agcccgcagg tgcatcccca agaatgtccc    4320
cggcgcagac tggcgcgtgc tggaggagat tgtgcggaag gaccccaccc gcgagaagtt    4380
caacgtgagc ccccccgcgg tacctgtgct ctgcatgctg ggtggtttgg acccagcgca    4440
tggtgggcag ggctgcacgt gcgtgggacg tgatgcgctt gggccaccgc tgcacgtcct    4500
cggtctcgct gcgtgctgca aatcatactc aaatcgtgca gttttggctg cacatggcgt    4560
tttgtaaggg tttcggggtg ttttcaacct ttccttgggt gtgcagtgca tccgccccag    4620
cggggcccac ccttcatgtg ccggtccctg cagggtcagc ccctggtgcc ttggtgcctg    4680
cccaacaccg ctgacaggca caacggctgg cgcggcctgt ttgggcgcct ggacctgaac    4740
gggcacttcc ccacctccac caccgacccc cagcccatgg gcaaggtgag ggggagaggg    4800
gcacagaacg gggggggttcc ggggggaggct caaagtctat ggagggtgta ggtgtcaaag   4860
ctgaaccctg gctgaggaga cggaggaggg ggggtggagg agtgcgtgtt caacctggcg    4920
cagtggtaca gctcctgttg tgtgtaccgt gctgggggcct gcatgcggcc tcccccaggc    4980
aacagctggg aacgttgcct ggcaccaaag ggcgccactg gaagacggag aggtgcagct    5040
cttgagaggt gcgcagctgt cgtttgccgt gcggatgcgg aggcatgggc gcgcgcgtgg    5100
caacacaggg aacaaagtgg aaggtgtgtc caccacccct cctgcaggtg gggcaggtgt    5160
```

-continued

```
tccaccccga gcaagatcgc atcgtgtctg tgcgggagtg cgcccgcgca caggtgagac    5220
cagcagcagg cacagcaccg gcggtgccac accatccaca ggccggtgcc ctgggaccac    5280
gctcaattgc tcagcagtgt gcgtgtgtgt gtgtgtgtgt ttgtagggga ggtcgcaggc    5340
cccaccccat ggtcccattc cctggggacg ctcatgcggt cacactcaca gtggcccgca    5400
cacccagtgc tcacctgctg ctggtgctgt ggctgcaggg cttccccgac cgcttccgct    5460
tctacggcaa cgtgcacagc aagcacaggc aggtcggcaa cgcggtgccg ccgcccctgg    5520
ctgccgcgct gggcaggcag ctgcgcaagg tgagtccgcg cagcgcgcac agcacggagg    5580
caagctccac acagtgactg ccgcgcgcga cgtgtggta cgtgcactgc atggccgcg    5640 cacggcaagg ccggggttgg tggtgccaat gcattttgg ttggcggcaa ttgtttcgct    5700
cctgctggtg cttcagtcgc ttttgcggtg cgccgcaaac ataaaggtgc cttctggtgg    5760
gggcgcgctg caggccttgg agctgaaggc ctcggaggag gccaaggaga ggatccaggc    5820
gcatctgaag gggttgtag                                                 5839
```

<210> SEQ ID NO 5
<211> LENGTH: 258
<212> TYPE: PRT
<213> ORGANISM: Parachlorella sp.
<220> FEATURE:
<221> NAME/KEY: misc_feature
<223> OTHER INFORMATION: Protein_EMRE3EUKT596408 methyltransferase

<400> SEQUENCE: 5

```
Met Gln Val Ala Gly Gly Glu Gly Gly Gly Ala Ser Ala Arg Gly
1               5                   10                  15

Leu Leu Glu Ala Arg Arg Glu Arg Ala Ala Ala Gly Val Pro Leu Lys
                20                  25                  30

Trp Arg Ser His Val Lys Val Pro Arg His Ala Pro Leu Pro Arg Leu
            35                  40                  45

Thr Val Arg Asp Val Ile Gly Asp Leu Pro Glu Glu Val Gly Pro Gly
        50                  55                  60

Leu Val Pro Tyr Ala Arg Asp Pro Pro Ser Phe Phe Ala Arg Ser Met
65                  70                  75                  80

Arg Ser Ala Gly Ser Glu Gln Gly Val Ser Asn His Gln Ile Trp Gly
                85                  90                  95

Leu Ser Ala Glu Asn Arg Gln Arg Cys Ala Ala Val Pro Leu Gly Gly
            100                 105                 110

Asp Pro His Tyr Pro Gly Cys Ala Ser Trp Glu Gly Ala Ser Gly Val
        115                 120                 125

Thr Glu Asn Pro Phe Val Pro Ala Arg Ala Gly Asp Trp Arg Asp Leu
    130                 135                 140

Pro Pro Glu Leu Gln Pro Ala Gly Met Gln Gln Leu Ala Arg Asp
145                 150                 155                 160

Gly Lys Asp Phe Ala Gly Val Tyr Gly Arg Leu Ile Trp Gly Gly Gln
                165                 170                 175

Phe Ser Thr Leu Leu Thr Asn Pro Asn Leu Asn Ser Asp Thr Thr Met
            180                 185                 190

Cys Phe Ile His Pro Ser Ala Pro Arg Pro Leu Ser Cys Ser Glu Ala
        195                 200                 205

Ala Arg Val Gln Gly Thr Pro Asp His Val Glu Phe Lys Gly Thr Ile
    210                 215                 220

Ala Glu Val Tyr Arg Gln Ile Gly Asn Ser Val Pro Val Pro Leu Gly
225                 230                 235                 240
```

Ala Ala Leu Gly Arg Glu Leu Ile Met Ala Leu Lys Gln His Ala Arg
            245                 250                 255

Val Thr

<210> SEQ ID NO 6
<211> LENGTH: 777
<212> TYPE: DNA
<213> ORGANISM: Parachlorella sp.
<220> FEATURE:
<221> NAME/KEY: misc_feature
<223> OTHER INFORMATION: Protein_EMRE3EUKT596408, cDNA for SEQ ID 5

<400> SEQUENCE: 6

```
atgcaggttg ctgggggtga gggcgggggt ggggcttctg caagagggct gctggaggcc      60
aggcgggaga gggcagccgc gggtgtcccc ctcaaatggc gcagccacgt caaggtgccc     120
cgccatgcgc ccctccccg cctgacagtg cgggacgtga ttggagacct gccggaggag     180
gtgggcccag gctggtgcc ctacgccagg atcccccga gcttctttgc tcgcagcatg     240
cgcagcgcgg gatctgagca aggcgtgtcc aaccaccaga tctgggggct cagcgccgag     300
aatcggcagc ggtgtgcggc ggtgccactg ggggagacc cccactaccc gggctgtgcc     360
tcctgggagg gggccagcgg ggtgacagaa aaccccttcg tccctgccag gcgggagac     420
tgagggatc ttcccccaga gctgcagcct gccggcatgc agcagcagct ggcccgggac     480
ggcaaggatt ttgcaggcgt gtatggccgg ctgatctggg gagggcagtt ctccacgctg     540
ctgaccaacc caaacctgaa cagcgacacg accatgtgct tcatccaccc ttctgcaccg     600
cgcccgctca gctgcagtga ggcagccaga gttcagggta cacctgatca cgtggagttc     660
aaaggcacga ttgcagaggt gtatagacaa atagggaatt ctgtaccggt gccactgggg     720
gccgcgttag aagggagct gattatggca ctgaagcaac atgcaagagt cacgtga       777
```

<210> SEQ ID NO 7
<211> LENGTH: 376
<212> TYPE: PRT
<213> ORGANISM: Parachlorella sp.
<220> FEATURE:
<221> NAME/KEY: misc_feature
<223> OTHER INFORMATION: Protein_EMRE3EUKT596208 methyltransferase

<400> SEQUENCE: 7

Met Gln Gly Val Glu Leu Ile Arg Glu Leu Gln Pro Glu Tyr Ile Thr
1               5                   10                  15

Leu Glu Glu Val Pro Gln Phe Met Phe Val Arg Leu Pro Ala Gln Arg
            20                  25                  30

Ile Ala Ser Gly Cys Ala Arg Gln Leu Gln Gly Pro Ala His Gly Ser
        35                  40                  45

Leu Glu Asp Cys Lys Ser Leu Leu Val Arg Pro Trp Leu Trp Val Val
    50                  55                  60

Pro Gln Leu Leu Met Met Gly Tyr Gln Val Asp Val Arg Ile Leu Asn
65                  70                  75                  80

Ser Ala Arg Tyr Gly Thr Pro Gln Asp Arg Lys Val Thr Pro Arg Ser
                85                  90                  95

Thr Ser Arg Thr Asp Leu Cys Cys Lys Val Arg Lys Asp Ala Ser Gln
            100                 105                 110

Ala Ser Ser Thr Ser Val Ser Gln Gln Ile Arg Arg Asp Gln Leu Tyr
        115                 120                 125

Glu Gln Arg Phe Arg Val Ile Asp His Ala Gln Arg Val Trp Ala Gly

```
            130                 135                 140
Ile Ser Leu Gln Ile Glu Gly Leu Gln Leu Pro Pro Ala Val Thr Met
145                 150                 155                 160

Trp Glu Ala Ile Gly Asp Leu Pro Pro Leu Ile Lys Ser Asp Pro Cys
                165                 170                 175

Ser Thr Leu Ser Val Leu Ser Leu Pro Ala Trp Gln Pro Gln His Cys
            180                 185                 190

Ala Lys Lys Glu Ala Ala Gly Asp Val Gln Gln Pro Ala Leu Gly Arg
        195                 200                 205

Ser Pro Leu Gln Tyr Arg Pro His Ala Arg Leu Ser Ser Phe Val Gln
    210                 215                 220

Tyr Met Leu Arg Gly Ser Gly Arg Asn Leu Leu His His Gln Thr Arg
225                 230                 235                 240

Lys Trp Lys Gly Arg Val Ser Gln Ser Arg Lys Asp Arg Ala Phe Pro
                245                 250                 255

Thr Ile Cys Thr Val Tyr Asn Pro Ile Val Arg Asp Gly Thr His Pro
            260                 265                 270

Val Glu Pro Arg Leu Phe Ser Leu Ala Glu Arg Lys Arg Ala Gln Gly
        275                 280                 285

Ile Pro Asp Cys Val Gln Trp Ala Gly Ser Leu Ser Asn Gln Glu Arg
    290                 295                 300

Gln Val Gly Asn Ala Val Ala Trp Pro Met Ala Arg Ala Val Ala Cys
305                 310                 315                 320

Ala Ile Leu Ser Ala Ala Thr Gly Asn Val Thr Ser Asp Pro Ile Pro
                325                 330                 335

Thr Leu Asn Gly Ala Arg Arg Val Pro Leu Ile Ser His Val Phe Arg
            340                 345                 350

Val Glu Leu Gly Ser Gln Leu Gly Lys Gln Phe Phe Gln Ser Ala Ala
        355                 360                 365

Lys Cys Gly Met Ser Gly His Asn
    370                 375

<210> SEQ ID NO 8
<211> LENGTH: 1131
<212> TYPE: DNA
<213> ORGANISM: Parachlorella sp.
<220> FEATURE:
<221> NAME/KEY: misc_feature
<223> OTHER INFORMATION: Protein_EMRE3EUKT596208, cDNA for SEQ ID 7

<400> SEQUENCE: 8
atgcagggcg tggagcttat cagggagctg cagccagagt acatcactct agaggaggtg      60
ccacagttca tgttcgtccg tctgccagct cagaggatcg catcaggttg tgctcggcag     120
ttgcaaggcc cagcacatgg atcattggag gattgcaaaa gcttgttagt gcggccatgg     180
ctgtggggtg taccacagct gctgatgatg ggttaccagg tggacgtcag gatattgaac     240
tctgcccgtt atggaacccc gcaggacagg aaggttactc ctcgttccac atcgcgtact     300
gatctttgct gcaaggtgcg gaaggatgct tcccaagcct ccagcacctc agtatcacag     360
cagatacgga gggatcagct ttatgagcag cgattcagag taattgatca tgctcagaga     420
gtctgggcag gaatatccct gcagatcgag ggcctgcagc tgccccagc tgtgaccatg      480 tgggaggcca tagggattt accacccctg atcaagtccg acccttgcag tacgctgtct     540
gtcctgtctc tgcctgcttg caaccacag cattgtgcca agaaggaggc agcaggagat      600
gtgcagcagc cggcgcttgg gaggagcccc ttgcaatacc gtccacatgc caggctgagc     660
```

```
agctttgtgc aatacatgct acggggctca gggcgcaatc tgctgcacca ccagacacgc    720
aagtggaagg ggcgtgtttc gcagtcgagg aaggacaggg ccttccccac gatctgcaca    780
gtatacaatc ctatagtcag agacggcaca catcctgttg agccaaggtt gttttcatta    840
gctgagcgca agcgtgcaca aggaatacca gactgtgtgc agtgggctgg cagtctctca    900
aatcaggagc gacaagttgg caatgctgta gcatggccca tggcgagggc tgtggcatgt    960
gctattctca gtgcagctac aggcaatgtc acaagtgatc cgataccaac tctaaacgga   1020
gctaggcgtg taccactaat cagccatgtt tttcgagtcg agcttggcag ccagctggga   1080
aagcagtttt tccaaagtgc agctaaatgt ggcatgtctg gacacaattg a            1131
```

<210> SEQ ID NO 9
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: EMRE3EUKT598198_chimeric_gRNA

<400> SEQUENCE: 9

```
gggauucuca aagguguagc guuuuagagc uagaaauagc aaguuaaaau aaggcuaguc     60
cguuaucaac uugaaaaagu ggcaccgagu cggugcuuuu uuu                     103
```

<210> SEQ ID NO 10
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: RNA_ EMRE3EUKT590754_chimeric_gRNA

<400> SEQUENCE: 10

```
gcuagcgaca gccgucuugg guuuuagagc uagaaauagc aaguuaaaau aaggcuaguc     60
cguuaucaac uugaaaaagu ggcaccgagu cggugcuuuu uuu                     103
```

<210> SEQ ID NO 11
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: RNA_ EMRE3EUKT596408_chimeric_gRNA

<400> SEQUENCE: 11

```
cgugauugga gaccugccgg guuuuagagc uagaaauagc aaguuaaaau aaggcuaguc     60
cguuaucaac uugaaaaagu ggcaccgagu cggugcuuuu uuu                     103
```

<210> SEQ ID NO 12
<211> LENGTH: 103
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: RNA_ EMRE3EUKT596208_chimeric_gRNA

<400> SEQUENCE: 12

```
ggaguaaccu uccuguccug guuuuagagc uagaaauagc aaguuaaaau aaggcuaguc    60
cguuaucaac uugaaaaagu ggcaccgagu cggugcuuuu uuu                    103
```

<210> SEQ ID NO 13
<211> LENGTH: 2667
<212> TYPE: DNA
<213> ORGANISM: Parachlorella sp.
<220> FEATURE:
<221> NAME/KEY: misc_feature
<223> OTHER INFORMATION: Bleomycin resistance gene with introns, codon-optimized for Parachlorella

<400> SEQUENCE: 13

```
atggccaaac tgacatccgc tgttcctgtg ttgacagcaa gagatgttgc aggtgcagtg    60
gagttttgtg agttctgaga agctgattgt tgtttaactt cttttgaaagc tttatcgaag   120 attctgcaag cgatgaacat tgcttgtcaa gaccgagagc tgcatgccca cttgacatcc   180
agctttgaac ggctcttcat gtttgatttg tttctgattg tagggacaga tagactgggg   240
tttagcaggg actttgtgga ggacgatttt gcaggagtgg tgagggatga tgtgacactg   300
tttatctcag cagtgcagga tcaagtgagt gcagcgtcag ctgtggcagt tgttggcttt   360
cgtctcagtc agtagtttgc tgggattgat tatggagggc acagttgcaa ttttgagttg   420
cacgttgcga caagcgtgtt gacaaagcgt ggtcaagccg ccagtcttg ccggtggcgg    480 gtggcttggt ctaacttccg ctctacagca atcgttttgt tcatggttac ggggctggcg   540
tgccagaaag tcctggtcag ccaccctcgc ttcaaagccg tagcccaaca actttgcgaa   600
tatgttcgat ttgcaggtgg tgcccgataa tacactggca tgggtttggg tgagaggtac   660
agctctgcgt gcaacaggtt gcaagatgca gcgcaggtct tccctggtca acgatgtat    720 gcagagttga gaggcacttg agctgggtga atggcgtggg ctcgtaggta gtgtgcaggg   780
caggaagggc agccaatttt ggagttgtgg tccggtgtcg ttgcttcgag ccttattagg   840
actcttgctc atcaaagcgt tagttgtgaa taagttgatc tgaaaggatg ttatgtacag   900
caagcagcag cagttaagag tctggggagt agctgcacag ggcgaggtgt caagatggga   960
agggtcctgc ctccttatgt gttttttccct gtagggagg aagcctctta tgggcaatgg  1020
ttgggcatat tttccagcca gcccttcttt ctataggggc cagggtgggc ccagctcgtc  1080
ttggcttcca ccaccaggag agtgagggca ttgaagggcc ataaatagtc ctcccatcta  1140
cgtgcaccag agggtgtcgt ctaggctgtg catgccacga ggggaaggag ccaagaatga  1200
gtgtatgggt tgttttcatg tttaggctgg gataaaactg tttttcaattg cgcctgccgg  1260 gtgaaaacca cagcagcatc agcaagcttg gagaaggcca gcccgcccag cacaggctca  1320
cgttcccact caggcggtca gtcgggcggg ggtgtgagtc aggcaggcga gggtgtctgt  1380
gcctgacatc agcaccctctg cttagccact gcagccctg gagcagggta gggcgtcatt   1440
tgcagcaatc acctgctgcc tcacacgtcg cagcttggaa tttcaacgac catcagcgct  1500
ggggttgttg agggatcata gcagattttg gtgcagcctg gttgtcatgc tctttgtgga  1560
atggcctcta tgttcgagca attcgttgga tgttgaggtg cttggggaca gagagtcgaa  1620
tgatgggcca gggtcaaaca tgcgagcgtt tggctgagtc agcggttttt gctggtcact  1680
ttttcttttg tttcttattt aggtttgatg gatgtgtttt gtgctgctgc cctgaagctg  1740
cagcagcgtg tctgccctgc gctactgcgg gcaccaaggc tatgtgctgg tgcactcggc  1800
tgcgctgcac ctgtgcacct cgcactccgt ccagcctcca tgcagcacac gtactcacgg  1860
```

```
tgtcctcctg acctgtcgta cgctattcca aacttgctct tttgctgccg ctgctctcgt    1920
acacaattgc tgttgattat cgatatctaa tcgagcgcct gctgactgaa ctccgcaggt    1980
ttggatgaac tgtatgcaga gtggtctgaa gtggtgagca ccaactttag gtgggtgggc    2040
tctgaaggag gaggagggag cggggtgatta acagggcct gcatgaagag gagcagggggc   2100 tgcatggaca gcaggggaa ggtgcagaag ggagggtcaa gcggggttca ggtggctgtg     2160
ggtttctgca cgagcagtga agaagctgt atccttccac ctgctttcac tggcgaaagg    2220
ttgaaaacag gatgtcgcag ctggaaagat gttgcgctgt caagtgcaag ccatggttga    2280
gggtatgcct gtgtgcatgt gcttcttaaa gttactcctg ttctatggtt ctgggtgctt    2340
gttgtttgtg gtgcagggat gcaagcggac ctgcaatgac agagattgga gaacaacctt    2400
ggggaaggga gtttgcattg agagatcctg caggtgaggg ggcatgtaag caatggcagg    2460
caattcaaga acgaatcatt gctgcaaatg ctgggatggt atgcagctga ggtatctatt    2520
gccttgtatt ttgtctcgca ttgcatcggt ggtgcgttct gtggcctgag gcacagttct    2580
tgctgtttga taagggttcg actgagttgt cgtgtgtgct gtgctgcagg caattgcgtg    2640
cactttgttg cagaagaaca ggactga                                        2667

<210> SEQ ID NO 14
<211> LENGTH: 531
<212> TYPE: DNA
<213> ORGANISM: Parachlorella sp.
<220> FEATURE:
<221> NAME/KEY: misc_feature
<223> OTHER INFORMATION: RPS4 promoter

<400> SEQUENCE: 14
ccaccatggg ggaggtttga agtgtgcgcc tgatataatc atacacctaa aagcaccact      60
tgctgattgt gaagggacta tgtcgtttat gacgggacgt tacgctggcc gatggtttga    120
atttggacgc tgtggtagaa tgttatatgg acgtaaaggt tggcatattg aaaatcgtct    180
tcacaggcaa acttctagac gtgtgaccca ccggtaaaac gacaagcgtg gcgcgtcgat    240
tgcgctttga acgtcgtttg ttggactcca gatgaacctc aaaatcaaag cggtgattga    300
cgaaaatcaa atgacagccc gcaaaatttc atcagccttc ggatcggatt ctcagaatct    360
gattgtccct gctggctaca tttatgaaat ttcgtacatt ttggcagaaa tgtcccaata    420
ccatagcact gccgcctgag ctcacccgag caatgcatac tgggtacctc gcccatctcg    480 ccctcttttcc aagcccagtg ctgttgtaaa tagccaaagg gctcagtaac a            531

<210> SEQ ID NO 15
<211> LENGTH: 546
<212> TYPE: DNA
<213> ORGANISM: Parachlorella sp.
<220> FEATURE:
<221> NAME/KEY: misc_feature
<223> OTHER INFORMATION: RPS4 terminator

<400> SEQUENCE: 15
gcatagcatc agcctgtggc agggttgtgg tagggctgag tggcagggtt aaagggggttg     60 cctaccccac ccctactctc atgacaccag caacagcagc agctcatgca gtactcaaat    120
cactgatgtc aatggtgtga cacatttggt taaggctgct ttttaaagtg ctgctttggg    180
ggcagtgact gtgcagagct tggagcgtat ccccatgtaa tcagaaccga cgagagttcg    240
gggcaacctt tcatcttcac atttttttgtg atcagctaca gagtctgaaa tcaaatagag    300
```

```
gctgccatct aaacgcagga gtcacaacga aggcgaaaac tccaattgct gtactcaatg      360
cactaagtga ttgttcaatg gataaataca ctatgctcaa ttcatgccag cagagctgct      420
ccttccagcc agctacaatg cttttttcca cgccttttga agtatgaatg ttcagcttgc      480
tgtgcttgat gcatcaccat aaacacaatt ctacaacatt tcatgccaac aacagtacgg      540
gctttc                                                                 546
```

```
<210> SEQ ID NO 16
<211> LENGTH: 572
<212> TYPE: DNA
<213> ORGANISM: Parachlorella sp.
<220> FEATURE:
<221> NAME/KEY: misc_feature
<223> OTHER INFORMATION: ACP1 promoter

<400> SEQUENCE: 16
agtttgcata gttaagtatg ctggctattg cagtacctta tatgcaaaca agtgctcaat       60
ctgtttcatc attgtctgtg ggcaaattgc ctgccaatat tctccagtta ttgcctgttg      120
tttcaaatga ttgaaattgg aagttgtatt gctctacatt tttgacttgt gattttttca      180
tttgttgata tctgacaact gtgaactgca ctgaacttgc tgtgcttata aatgcatttt      240 tttgtttttgg gccacgttga ttccttgtga tactttcctg ctatcaaacc aaaaatatac      300
tctcatgact gacgtgcaac aaatgcatgg aagctttcaa cgttacgaca gctgcttgcc      360
ccccatcagc tattctacat gtgtaaccta ccttgcatgg ccaccacaac gctactgcat      420
gcaagatctg gcgcaactgg atgtcccaat agtagaagta tccggattat ctccgagagt      480
tttacatatg taatcgacgc catttctgtc atcaactata aatccattgc tcctgcattt      540
ctggcactga cattctacca caagcaatac ca                                    572
```

```
<210> SEQ ID NO 17
<211> LENGTH: 699
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: TurboGFP gene

<400> SEQUENCE: 17
atgttggaga gcgacgagag cggcctgccc gccatggaga tcgagtgccg catcaccggc       60
accctgaacg gcgtggagtt cgagctggtg ggcggcggag agggcacccc cgagcagggc      120
cgcatgacca acaagatgaa gagcaccaaa ggcgccctga ccttcagccc ctacctgctg      180
agccacgtga tgggctacgg cttctaccac ttcggcacct accccagcgg ctacgagaac      240
cccttcctgc acgccatcaa caacggcggc tacaccaaca cccgcatcga aagtacgag      300 gacggcggcg tgctgcacgt gagcttcagc taccgctacg aggccggccg cgtgatcggc      360
gacttcaagg tgatgggcac cggcttcccc gaggacagcg tgatcttcac cgacaagatc      420
atccgcagca acgccaccgt ggagcacctg cacccatgg gcgataacga tctggatggc      480
agcttcaccc gcaccttcag cctgcgcgac ggcggctact acagctccgt ggtgacagc       540 cacatgcact tcaagagcgc catccacccc agcatcctgc agaacggggg ccccatgttc      600
gccttccgcc gcgtggagga ggatcacagc aacaccgagc tgggcatcgt ggagtaccag      660
cacgccttca gacccccgga tgcagatgcc ggtgaagaa                             699
```

<210> SEQ ID NO 18
<211> LENGTH: 869
<212> TYPE: DNA
<213> ORGANISM: Parachlorella sp.
<220> FEATURE:
<221> NAME/KEY: misc_feature
<223> OTHER INFORMATION: ACP1 terminator

<400> SEQUENCE: 18

```
gcagcagctt gttatgcctt ccccatgggc atcagcatgc tgcaagctgt ctagatatcc    60
agctttcagt ggaggttgag cgagggtcag cagcggttcc ctggcgatgg cggtcagctt   120
ttctggaagc cttcactagg actgcgccca gcgcatgtga cgccaatcga acttgtgtgc   180
aaggccaaat tttgtgaccc tgtgctgcac ttcatgtatt caagaattga aagaaattt    240
cattgctgcc cttctttcac tttaatttcc atccctggat ccacctccca ccattgtggt   300
tgatgggtag gggttttggg taggtgcagt tcgttgtgca cgttgacatg tgtaacggtg   360
agcaaaggaa ttgctgggca agtagctatt gcagcttaag ggcatggtga aacacttgtg   420
ctgtatttac agaggaagcc agacaggtaa ggagtgtgtg gcagcttgga acaggagggc   480
tggtcgcaac aagtatgcat atcccatgat tgttgacata agagcagcag gtgcatattg   540
ccagcctttg tgaaagtgga ttgaaaatcg attagttggt gtgatagctg aggctaggca   600
ctgccaacct gcagtgaaat gaggctccaa gaccgggtaa taatacaggc aatcgaatcc   660
agttgaaatt acggcgatta aatccaagcg agcgttgtaa gaacatctgc acctgtctga   720
agtagtgagc ggataatgag cattgcttgc cttctatcac tatacctgac agttacgtgt   780
cacacactct caagcacaac acacagcggc aaagttactt gctaaacctc acagtcaagc   840
tgaaaataaa ggctaaatta cgtgagacc                                    869
```

<210> SEQ ID NO 19
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST106, primer

<400> SEQUENCE: 19

```
gtgtgggtgc tctggatcag ccatcgat                                      28
```

<210> SEQ ID NO 20
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST107

<400> SEQUENCE: 20

```
tgagaaagca agctgtgcag gagctcagg                                     29
```

<210> SEQ ID NO 21
<211> LENGTH: 31
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<210> SEQ ID NO 22
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST078, primer

<400> SEQUENCE: 21
gcgtgcactt tgttgcagaa gaacaggact g         31

<210> SEQ ID NO 22
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST258, primer

<400> SEQUENCE: 22
gtgtcatctt cagtgccacc ctctttccgc         30

<210> SEQ ID NO 23
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA oligoST259, primer

<400> SEQUENCE: 23
ctagcagcag cagcctcaat atgctgctgc         30

<210> SEQ ID NO 24
<211> LENGTH: 30
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST108, primer

<400> SEQUENCE: 24
cagaattctt agctgtgccc cagtgcatgg         30

<210> SEQ ID NO 25
<211> LENGTH: 29
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST109, primer

<400> SEQUENCE: 25
ctccaagctt gatcacagct cgccacatc         29

<210> SEQ ID NO 26
<211> LENGTH: 27
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST110, primer

<400> SEQUENCE: 26
gccgcgcact tcacctgtac agaccgt    27

<210> SEQ ID NO 27
<211> LENGTH: 28
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: DNA_oligoST111, primer

<400> SEQUENCE: 27
ctgcaggaca gcagttgctg aacttgcc    28

<210> SEQ ID NO 28
<211> LENGTH: 1612
<212> TYPE: PRT
<213> ORGANISM: Oocystis sp.
<220> FEATURE:
<221> NAME/KEY: misc_feature
<223> OTHER INFORMATION: EMRE3EUKT2030386 methyltransferase

<400> SEQUENCE: 28

Met Ala Ser Lys Gln Cys Ala Asn Ser Ser Gly Gln Val Ala Ala Gly
1               5                   10                  15

Arg Gly Ala Ala Ser Ala Phe Glu Ala Ala Ala Ala Ser Gly Ser
            20                  25                  30

Asp Ala Ser Gly Ser Asn Val Pro Leu Pro Met Pro Arg Val Pro Ser
        35                  40                  45

Leu Leu Ser Lys Val Met Thr Leu Gly Gly Gln Ala Leu Ser Lys Val
    50                  55                  60

Val Gly Ser Pro Ala Arg Cys Gly Ser Ala Ser Ser Ala Glu Pro Ala
65                  70                  75                  80

Gly Ser Ala Ala Pro Ile Ala Leu Glu Pro Ala Thr Ser Thr Gln Ala
                85                  90                  95

Ser Ser Pro Glu Gln Cys Pro Gly Arg Ala Ala Lys Arg Lys Ala Ala
            100                 105                 110

Glu Arg Ile Ser Gly Glu Ala Ala Thr Thr Ala Ala Leu Phe Pro Ser
        115                 120                 125

Gly Ser Val Pro Gly Ser Ser Pro Arg Lys Arg Arg His Arg Pro Gly
    130                 135                 140

Ala Gly Ala Ala Gly Glu Glu Gly Gln Ala Gln Gly Gln Ala Gln Gly
145                 150                 155                 160

Gln Ala Arg Pro Pro Arg Ala Pro His Ala Asn Arg Ala Ala Ala Ala
                165                 170                 175

Thr Arg Arg Ala Ala Gln Gln Gln Gln Gln Gln Gln Gln Gln Gln Gln
            180                 185                 190

Gln Gln Asp Asp Val Trp Cys Asp Glu Asp Gly Thr Ala Ala Ala Gly
        195                 200                 205

Gly Pro Cys Trp Thr Val Pro Gln Val Glu Arg Arg Leu Lys Glu Thr
    210                 215                 220

Pro Ser Trp Phe Lys Ala Glu Asp Asp Asn Asp Glu Tyr Leu Pro Glu
225                 230                 235                 240

Gln Tyr Met Asp Gln Arg Tyr Arg Ala Leu Gly Gly Pro Ala Gly Val
                245                 250                 255

Ala Phe Met Ala Cys His Trp Leu Asp Arg Glu Val Ala Gly Tyr Thr
            260                 265                 270

```
Trp Gly Ala Arg Ile Ser Lys Asp Glu Ala Gln Arg Trp Pro Asn
            275                 280                 285
Arg Ala Met Cys Glu Cys Ser Ala Ala Thr Val Lys Glu His Ile Ser
        290                 295                 300
Lys Arg Met Ser Arg Glu Gly Lys Pro Thr Asp Glu His Phe Trp
305                 310                 315                 320
Asp Phe Ala Thr His Gly Ala Phe Pro Ala Met Ala His Phe Glu Glu
                325                 330                 335
Val Thr Ile Arg Arg Glu Gly Glu Gln Pro Phe Thr Ala Arg Leu Gly
            340                 345                 350
Asp Asn Ile Glu Leu Asp Ser Ser Asp Gln Leu Leu Glu Gly His Leu
        355                 360                 365
Gln Arg Leu Gly Ile Ser Arg Gln Gln Leu Ala Gly Met Asp Pro Gln
    370                 375                 380
Asp Arg Pro Ser Thr Lys Trp Val Met Gln Val Asp Glu Leu Phe Gln
385                 390                 395                 400
Asp Ile Thr Gly Gln Arg Val Val Ser Gly Thr Trp Tyr Tyr Ser Pro
                405                 410                 415
Arg His Thr Ala Ile Met Cys Glu Pro Ser Arg Arg Val Thr Lys Ala
            420                 425                 430
Lys Ala Ala Thr Ala Ala Ser Lys Asn Ala Val Gly Lys Thr Ser Thr
        435                 440                 445
Gln Gly Gly His Glu Ser Glu Gly Glu Glu Glu Asp Ala Glu Glu
    450                 455                 460
Glu Glu Tyr Pro Gly Tyr Val Pro Val Asp Phe Asp Pro Arg Leu Leu
465                 470                 475                 480
Phe Arg Ala Thr Val Trp Asp Asn Glu Arg Tyr Gly Met Thr Asp Gln
                485                 490                 495
Leu Leu Glu Val Val Glu Arg Val Thr Val Gly Asp Ala Val Pro
            500                 505                 510
Gly Lys Pro Pro Pro Glu Asp Cys Asp Tyr Tyr Cys Ser Met Val His
        515                 520                 525
Asp Arg Arg His Tyr Thr Phe Ala Asp Ser Val Thr Asp Gln Pro Pro
    530                 535                 540
Ser Lys Ala Lys Trp Ala Asn Thr Lys Arg His Leu Tyr Val Leu Asp
545                 550                 555                 560
Leu Tyr Ser Gly Cys Gly Gly Leu Ser Glu Gly Leu Asp Thr Asp Ser
                565                 570                 575
Asp Arg Leu Glu Ile Ser Thr Arg Trp Ala Val Asp Tyr Ala Ala Asp
            580                 585                 590
Met Ala Ala Thr Phe Arg Ala Asn Phe Pro Arg Ala Ala Met Tyr Asn
        595                 600                 605
Thr Gly Thr Asp Glu Phe Leu Leu Met Cys Lys Leu Phe Arg Ser Leu
    610                 615                 620
Tyr Gln Tyr Tyr Val Thr Gln Trp Ala Gly Pro Gly Ser Pro Leu Pro
625                 630                 635                 640
Pro Gly Glu Pro Gly Ala Pro Pro Gly His Arg Val Leu Arg Asp Arg
                645                 650                 655
Thr Asn Gly Gly Asn Ser Arg Asp Asp Val Ala Pro Arg Leu Gly
            660                 665                 670
Leu Glu Leu Glu Gln Asp His Pro Glu Cys His Pro Gly Ala Lys Ala
        675                 680                 685
Gly Thr Gly Gly Lys Ala Gly Gly Gly Gly Lys Ala Ala Arg Gly Ala
```

```
                690             695             700
Ala Ser Gly Ile Val Arg Asp Pro Ser Pro Leu Gly Gly Asp Ala Tyr
705                 710             715                 720

Gly Arg Asp Glu Glu Asp Lys Glu Gly Val Val Asp Tyr Ile Ala Asp
                725             730                 735

Ile Lys Leu Val Asp Arg Gly Gln Arg Gly Thr Ala Gly Gln Gln Lys
                740                 745             750

Gly Asn Leu Leu Arg Pro Leu Gly Gln Ala Glu Gly Glu Leu Leu Phe
            755             760             765

Leu Val Lys Trp Arg Gly Met Pro His Ser Arg Ala Thr Trp Glu Arg
770             775             780

Leu Ser Ser Met Gln His Val Pro His Lys Leu Arg Lys Phe Leu Phe
785             790             795                 800

Trp Cys His Ser Ser Lys Lys Ile Pro Leu Pro Gly Asp Val Gly Val
                805             810             815

Ile Thr Gly Gly Pro Pro Cys Gln Gly Ile Ser Gly Leu Asn Arg His
                820             825             830

Ala Gln Arg Ser Gly Val Leu Ser Asp Ser Arg Asn Arg Gln Leu Ser
            835             840             845

Ala Tyr Phe Glu Ala Val Glu Tyr Phe Arg Pro Ala Tyr Val Leu Met
            850             855             860

Glu Asn Val Lys Asp Ile Phe Ser Lys Glu Asp Gly Leu Tyr Ala Lys
865             870             875                 880

Ala Ala Gln Ala Glu Leu Leu Arg Leu His Tyr Gln Thr Arg Ile Gly
                885             890             895

Ile Ile Ser Ala Gly Asp Gln Gly Ala Pro Gln Gly Arg Trp Arg Cys
                900             905             910

Phe Phe Trp Gly Ala Lys Ser Gly Glu Glu Gln Leu Pro Pro Phe Pro
            915             920             925

Gly Pro Ser His Gln Pro Ile Thr Phe Asp Lys Ala Leu Pro Leu Glu
            930             935             940

Ala Gln Leu Tyr Cys Gln Val Lys Val Glu Glu Gln Arg Glu Gly Gln
945             950             955                 960

Pro Pro Arg Gln Leu Leu Pro Gly Thr Leu Leu Gly Asp Ser Leu Ser
                965             970             975

Asp Leu Pro Glu Val Thr Asn Phe Cys Ala Lys Glu His Ala Arg Tyr
                980             985             990

Thr Arg Glu Pro Asp Arg Pro Tyr Gln Ala Leu Met Arg Arg Asp Pro
            995             1000            1005

Gln His Trp Gln Thr Ser Arg Glu Glu Arg Asn Arg Leu Ala Arg
    1010            1015            1020

Glu Ala Met Gln Asp Asp Tyr Arg Gln Asn Asn Gln Ala Thr Val
    1025            1030            1035

Asp Thr Val Glu Met Leu Asn Ala Gln Gln Pro Gly Leu Gly Phe
    1040            1045            1050

Val Lys Leu Gly Tyr Thr Tyr Phe Cys Gly Lys Ser Trp Pro Val
    1055            1060            1065

Val Arg Leu Gly Gly Lys Asn Gly Lys Gly Lys Gln Val Val Val
    1070            1075            1080

Gly Gly Gly Gly Arg Gln Gln Arg Gly Val Lys Arg Ser Ala Ala
    1085            1090            1095

Gly Gly Cys Ser Ala Ala Ala Gly His Glu Gln Glu Glu Asp Glu
    1100            1105            1110
```

```
Asp Glu Glu Asp Asp Glu Glu Asp Ser Ser Asp Asp Asp Asp Glu
    1115                1120                1125

Asp Asp Glu Glu Glu Ala Gly Glu Asp Ala Glu Glu Glu Gly Leu
    1130                1135                1140

Pro Lys Gly Ser Thr Lys Glu Gln Gln Lys Gln Glu Lys Asp Phe
    1145                1150                1155

Ala Arg Gln Val Trp Leu Ala Ala Val Lys Glu Ile Ala Ala Thr
    1160                1165                1170

Gln Gly Pro His Ala Ala Leu Ala Gln Val Glu Met Ala Ala
    1175                1180                1185

Ser Arg His Ala Leu Ala Trp Ala Leu Gly Val Gln Val Tyr Lys
    1190                1195                1200

Glu Leu Ile Ala Ala Leu Glu Glu Pro Asp Cys Ala Pro Leu Arg
    1205                1210                1215

Asp His Arg Pro Leu Cys Val Asn Ala Asp Asp Tyr Leu Arg Cys
    1220                1225                1230

Ala Ala Val Pro Thr His Lys Gly Ala Asn Phe Arg Asp Met Lys
    1235                1240                1245

Gly Val Val Thr His Ser Gly Gly Glu Cys Cys Ala Gly His Thr
    1250                1255                1260

His Pro His Ser Lys Ser Gly Gly Ser Lys Gly Thr Lys Leu
    1265                1270                1275

Val Cys Pro Gly Gly Gly Thr Phe Trp Tyr Ala Lys Pro Ser Thr
    1280                1285                1290

Lys Lys Ser Ser Arg Val Asp His His Asp Lys Ile Gly Glu Arg
    1295                1300                1305

Val Thr His Lys Asp Gly Cys Asp Ala Arg Leu Phe Leu Leu Ala
    1310                1315                1320

Thr Gly Asp Leu Leu Cys Pro Arg Trp Cys Ile Thr Tyr Lys Lys
    1325                1330                1335

Gly Asn Ser Asn Gly Arg His Gly Cys Phe Gly Arg Leu Trp His
    1340                1345                1350

Asp Glu Ile Gln Pro Thr Val Val Gly Arg Val Glu Pro His Asn
    1355                1360                1365

Leu Lys Val Val His Pro Trp Gln Asp Arg Val Val Thr Met Arg
    1370                1375                1380

Glu Asn Met Arg Cys Gln Gly Phe Pro Asp Tyr Phe Val Leu Val
    1385                1390                1395

Gly Leu Ser Lys Ala Asn Ala Gly His Ser Trp Val Arg Asn Ala
    1400                1405                1410

Ser Phe Lys Gln Arg Tyr Gln Gln Ile Gly Asn Ala Val Cys Pro
    1415                1420                1425

Leu Val Ala Gly Ala Leu Gly Arg Cys Leu Ala Leu Ala Ala Leu
    1430                1435                1440

Gly Glu Ala Asp Ser Ser Arg Phe Val Leu His Val Pro Asp Pro
    1445                1450                1455

Glu Leu Glu Arg Val His Asp Leu Ala Ala Thr Arg Gly Trp Lys
    1460                1465                1470

Thr Tyr Ala Gln Glu Ala Gly Leu Leu Pro Ser Gly Val Gly Gly
    1475                1480                1485

Gly Leu Gly Arg Gly Leu His Arg Ser Gly Ser Val Gln Gly Ser
    1490                1495                1500
```

```
Gly Met Asn Leu His Leu Ser Ser Ser Ser Leu Gly Gly Gly
    1505                1510                1515

Leu Gly Ser Ser Gly Leu Gly Gly Gly Leu Gly Gly Ser Gly Leu
    1520                1525                1530

Gly Asp Gly Ser Gly Gly Arg Gly Ser Thr Gly Ala Gly Ala Ala
    1535                1540                1545

Gly Gly Gly Gln Ala Glu Glu Glu Leu Thr Leu Ala Leu Glu Leu
    1550                1555                1560

Ser Gly Asp Gly Asp Glu Gly Glu Glu Asp Glu Asp Gly Glu
    1565                1570                1575

Glu Asp Glu Asp Gly Asp Gly Glu Glu Gly Glu Glu Pro Arg
    1580                1585                1590

Gly Gly Asp Gly Ser Gly Glu Ser Asp Val Asp Glu Asp Glu Ser
    1595                1600                1605

Asp Leu Glu Asp
    1610

<210> SEQ ID NO 29
<211> LENGTH: 4839
<212> TYPE: DNA
<213> ORGANISM: Oocystis sp.
<220> FEATURE:
<221> NAME/KEY: misc_feature
<223> OTHER INFORMATION: EMRE3EUKT2030386, coding sequence of SEQ ID 28

<400> SEQUENCE: 29
atggcgtcca agcaatgcgc caactccagc ggacaagtgg cggcaggtcg cggcgccgca      60
tcggcgttcg aagctgcagc agcagcaagt gggagtgatg ccagcggaag caatgtgccg     120
ctgccgatgc cccgagtgcc cagcttgctg tccaaggtga tgacactggg aggccaagcg     180
ctgtccaagg tagtagggag cccagcacgc tgcggcagcg catcctcggc agaaccagca     240
gggtcggcag ccctattgc gttggagcct gccaccagca cccaggcctc cagcccagag      300
cagtgtcctg ggcgggcagc caagcgcaag gccgccgagc gcatctcagg cgaagcggcc     360
accaccgccg ctctgttccc aagcggcagc gtccctggct cctcgcctcg taagcgccgc     420
caccggcccg gggccgggc cgctggcgaa gagggtcagg cccagggtca ggcccagggt      480
caggcccgcc cccctcgggc ccctcacgca accgggccg ccgccgccac acgccgtgcc      540
gcacaacagc agcagcagca gcagcagcag cagcagcagc aggatgatgt ctggtgtgat     600
gaggacggca ccgctgctgc cggcgggccc tgctggaccg tgccgcaggt ggagcgcagg     660
ctcaaggaga cgccgtcctg gtttaaggcg gaggacgaca cgacgagta cctgcccgag      720 cagtacatgg accagcggta ccgcgccctg gcggcccgg ccggggtggc gttcatggcc      780
tgccattggc tggacaggga gtggcgggg tacacgtggg gtgcacgcat atccaaggac      840
gaagcgcagc gcaggtggcc aaaccgtgca atgtgcgagt gcagcgctgc tacagtgaaa     900
gagcacatct ccaagcgaat gagccgggag ggggaaagc ctaccgacga gcactttgg       960 gactttgcca cgcatggcgc gttccctgcc atggcgcact tgaggaggt gaccatccgc     1020 agggaaggcg agcagccatt cacggcgcgt ctgggcgata acatcgagct cgactccagc    1080
gaccagctcc tggaggggca cctgcagcgg ctggggatta gcaggcagca gctggcgggg    1140
atggacccac aggacaggcc atcgaccaaa tgggtcatgc aggtcgacga gctgttccag    1200
gacattacgg ggcagagggt agtgtccggg acctggtact actctccccg ccacaccgcc    1260
atcatgtgcg agccctctcg tcgcgtgacc aaggccaagg cagcaacggc agcctcgaaa    1320
```

```
aacgcggtgg gcaagacaag cacccagggc ggtcatgaga gcggagaggg ggaggaggag   1380
gatgcggagg aggaggaata tcctggctat gtccccgttg actttgaccc gcggctgctg   1440
ttccgggcga ctgtgtggga caacgagcgg tacggcatga cagatcagct actggaggtg   1500
gtggagaggg tggtgaccgt cggcgatgcc gtgcccggca agccaccccc ggaggactgc   1560
gattactact gctccatggt gcacgaccgc aggcactaca cctttgctga ctccgtcacc   1620
gaccagccgc cttcaaaggc caagtgggcg aacacgaagc ggcacctgta cgtgttggac   1680
ctgtactcgg gatgcggcgg cctgtccgag gggctggaca ccgactccga ccgactggag   1740
atcagcacgc ggtgggcggt cgactacgcc gctgacatgg cggccacctt cagggccaat   1800
ttcccccggg ccgcgatgta caacacgggc acggacgagt tcctgctgat gtgcaagctg   1860
ttccgctccc tgtaccagta ctacgtgacg cagtgggccg ggccgggcag cccgctgcct   1920
cccggggagc ccggagcccc ccctggccac agggtgctgc gggaccgcac caacggcggc   1980
aacagccgcg acgatgatgt ggcgcccagg ctgggcctag agctggagca ggaccaccct   2040
gaatgccacc cgggcgccaa agcgggcact ggaggcaagg cgggcggtgg aggcaaggcg   2100
gcaaggggg ccgccagcgg cattgtcaga gacccgtctc ccttgggggg agatgcttac   2160
ggcagggacg aggaagataa agagggcgtg gtggactaca tcgctgacat caagctcgtg   2220
gaccggggcc agcgcggcac tgcagggcag cagaagggca acctgctccg cccctcggt    2280
caggccgagg gtgagctgct gttccttgtc aagtggcgtg gcatgcccca ctctcgcgcc   2340
acatgggagc gcctgtcaag catgcagcac gtgccgcaca agctgcggaa gttccttttc   2400
tggtgccaca gctccaagaa gatcccgctg cccggcgacg tgggtgtcat cacgggcggg   2460
ccgcccctgcc agggcatcag cggcctcaac cgccacgcgc agaggagcgg cgtgctcagc   2520
gacagcagga accgccagct cagcgcgtac tttgaggcgg tggagtactt ccgtcccgcg   2580
tacgtgctga tggagaacgt caaagacata ttcagcaagg aggacggtct gtacgcaaag   2640
gccgcgcagg cggagctgct gcggctgcac taccagacgc gcatcggcat catctctgca   2700
ggcgaccagg gcgcgccgca gggtcgctgg aggtgcttct tctggggcgc caagagcggc   2760
gaggagcagc tgccgcccct tccgggggcca agccaccagc ccatcacctt cgacaaggct   2820
ctgcccctgg aggctcagct gtactgccag gtcaaggtgg aggagcagcg ggaggggcag   2880
ccgcccaggc agctgctgcc agggacgctg ctgggcgaca gcctgagcga cctgcccgag   2940
gtgaccaact tctgcgccaa ggagcacgcc cgctacacca gggagccgga caggccctac   3000
caggcactca tgcgcaggga cccgcagcac tggcagacct ccaggaggga gcgcaacagg   3060
cttgcgcgtg aggccatgca ggatgactac aggcagaaca accaggcaac ggtagatacg   3120
gtagagatgc tcaacgcaca gcaaccaggc ctgggcttcg tcaagctggg ctacacctac   3180
ttctgcggga agagctggcc agtcgtacgc ctgggcggca gaacggcaa gggcaagcag    3240
gtcgtggtgg aggaggcgg caggcagcag aggggcgtca agcgctcggc ggctggaggg   3300
tgctcggcgg cggcgggcca cgagcaggag gaggacgagg atgaggagga tgacgaggag   3360
gattccagcg acgacgatga cgaggatgac gaggaggagg cgggagagga cgcggaggag   3420
gaggggctgc ccaaggggag taccaaggag cagcagaagc aggagaaaga ctttgcgcgg   3480
caggtgtggc tggctgctgt caaggagatt gccgccaccc agggcccgca cgctgccgcc   3540
ctggcacagg tggagatggc ggcatccagg cacgcgctgg cctgggcgct gggcgtacag   3600
gtgtacaagg agctgatcgc tgcgctggag gagcccgact gcgcgccgct gcgcgaccac   3660
cgcccccctgt gcgtcaacgc ggatgattac ctgcgctgcg cggccgtgcc cactcacaag   3720
```

```
ggggcaaact tccgcgacat gaaggggggtc gtcacgcaca gcggcggcga gtgctgtgct    3780
ggtcacacgc acccgcactc caagtccggc ggcggcagta agggcaccaa gctggtgtgc    3840
cccggtggtg gcaccttttg gtacgccaag ccatcgacca agaagagcag cagggtggac    3900
caccacgaca agatcggcga acgagtgacg cacaaggacg gctgcgacgc tcgcctgttc    3960
cttctcgcca cgggcgacct gctgtgcccg cgctggtgca tcacctacaa gaagggcaac    4020
agcaacgggc ggcacggctg cttcggccgg ctgtggcacg acgagatcca gcccacggtg    4080
gtcgggcggg tggagccgca caacctcaag gtggtgcacc cctggcagga cagggtggtg    4140
accatgcggg agaacatgcg gtgccagggc ttcccggact actttgtgct ggtcggtttg    4200
agcaaggcaa acgcgggcca cagctgggtg cgcaacgcct ccttcaagca gcgctaccag    4260
cagatcggca acgcggtgtg cccgctggtc gcgggcgccc tgggccgatg cctcgccctg    4320
gcagccctgg gcgaggctga ctcgtccagg tttgtactgc acgtgccgga ccccgagctg    4380
gagagggtgc acgatctggc ggccaccagg gggtggaaaa cgtatgcaca ggaagcgggg    4440
ctgctgccca gcggcgtggg tggcggcctg ggcagaggcc tgcatcgcag cggcagcgtc    4500
cagggcagcg gcatgaacct gcacctcagc agcagcagct ccctgggcgg tggcctgggc    4560
agcagcggcc tgggcggtgg actgggtggg agcggcctgg gcgacggcag tggtgggcgt    4620
ggcagcaccg gggcagggc agccggggggt gggcaggcgg aggaggagct gacgctggca    4680
ctcgagttgt ctggggatgg ggatgaggat ggggaggagg atgaggatgg ggaggaggat    4740
gaggatgggg atggggagga gggcgaggag gagccacgcg gcggtgacgg cagcggtgag    4800
agtgatgtcg acgaggacga gagtgacttg gaggactga                          4839
```